US010194659B2

(12) United States Patent
Dubost et al.

(10) Patent No.: US 10,194,659 B2
(45) Date of Patent: Feb. 5, 2019

(54) ACTIVE COMPOUND COMBINATIONS

(71) Applicant: BAYER CROPSCIENCE AKTIENGESELLSCHAFT, Monheim am Rhein (DE)

(72) Inventors: Christophe Dubost, La Tour de Salvagny (FR); Ulrike Wachendorff-Neumann, Neuwied (DE); Simon Maechling, Lyons (FR); Ruth Meissner, Leverkusen (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 15/537,172

(22) PCT Filed: Dec. 16, 2015

(86) PCT No.: PCT/EP2015/080028
§ 371 (c)(1),
(2) Date: Jun. 16, 2017

(87) PCT Pub. No.: WO2016/097003
PCT Pub. Date: Jun. 23, 2016

(65) Prior Publication Data
US 2017/0339953 A1    Nov. 30, 2017

(30) Foreign Application Priority Data
Dec. 19, 2014   (EP) .................................... 14199123

(51) Int. Cl.
*A01N 43/40* (2006.01)
*A01N 43/56* (2006.01)
(52) U.S. Cl.
CPC ............. *A01N 43/40* (2013.01); *A01N 43/56* (2013.01); *A01N 2300/00* (2013.01)

(58) Field of Classification Search
CPC combination set(s) only.
See application file for complete search history.

(56) References Cited

U.S. PATENT DOCUMENTS 9,376,391 B2    6/2016  Maechling et al.
2009/0018015 A1  1/2009  Wachendorff-Neumann et al.

FOREIGN PATENT DOCUMENTS

WO    2014/095675 A1    6/2014

OTHER PUBLICATIONS

Leonard, P.K., "Resistance risk evaluation, 'a European regulatory perspective," Crop Protection, vol. 19, pp. 905-909 (2000).*
Issac, S., "What is the mode of action of fungicides and how do fungi develop resistance?" Mycologist, vol. 13(1), pp. 38-39 (1999).*
Rummens, F.H.A., "An improved definition of synergistic and antagonistic effects," Weed Science, vol. 23(1), pp. 4-6 (1975).*
International Search Report of PCT/EP2015/080028 dated Jan. 19, 2016.

* cited by examiner

*Primary Examiner* — John Pak
(74) *Attorney, Agent, or Firm* — McBee Moore Woodward & Vanik IP, LLC

(57) ABSTRACT

The present invention relates to active compound combinations, in particular within a fungicide composition, which comprises (A) a difluoromethyl-nicotinic indanyl carboxamide of formula (I) and a further fungicidally active compound (B). Moreover, the invention relates to a method for curatively or preventively controlling the phytopathogenic fungi of plants or crops, to the use of a combination according to the invention for the treatment of seed, to a method for protecting a seed and not at least to the treated seed.

16 Claims, No Drawings

ACTIVE COMPOUND COMBINATIONS

CROSS REFERENCE TO RELATED APPLICATIONS

This application is a § 371 National State Application of PCT/EP2015/080028, filed Dec. 16, 2015, which claims priority to European Application No. 14199123.2 filed Dec. 19, 2014.

BACKGROUND OF THE INVENTION

Field of the Invention

The present invention relates to active compound combinations, in particular within a fungicide composition, which comprises (A) a difluoromethyl-nicotinic indanyl carboxamide of formula (I) and a further fungicidally active compound (B). Moreover, the invention relates to a method for curatively or preventively controlling the phytopathogenic fungi of plants or crops, to the use of a combination according to the invention for the treatment of seed, to a method for protecting a seed and not at least to the treated seed.

Description of Related Art

It is already known that certain difluoromethyl-nicotinic indanyl carboxamides can be used as fungicides (see WO 2014/095675).

Since the ecological and economic demands made on modern active ingredients, for example fungicides, are increasing constantly, for example with respect to activity spectrum, toxicity, selectivity, application rate, formation of residues and favourable manufacture, and there can also be problems, for example, with resistances, there is a constant need to develop novel fungicidal compositions which have advantages over the known compositions at least in some areas.

SUMMARY

The present invention provides active compound combinations/compositions which in some aspects at least achieve the stated objective.

It has now been found, surprisingly, that the combinations according to the invention not only bring about the additive enhancement of the spectrum of action with respect to the phytopathogen to be controlled that was in principle to be expected but achieves a synergistic effect which extends the range of action of the component (A) and of the component (B) in two ways. Firstly, the rates of application of the component (A) and of the component (B) are lowered whilst the action remains equally good. Secondly, the combination still achieves a high degree of phytopathogen control even where the two individual compounds have become totally ineffective in such a low application rate range. This allows, on the one hand, a substantial broadening of the spectrum of phytopathogens that can be controlled and, on the other hand, increased safety in use.

In addition to the fungicidal synergistic activity, the active compound combinations according to the invention have further surprising properties which, in a wider sense, may also be called synergistic, such as, for example: broadening of the activity spectrum to other phytopathogens, for example to resistant strains of plant diseases; lower application rates of the active compounds; sufficient control of pests with the aid of the active compound combinations according to the invention even at application rates where the individual compounds show no or virtually no activity; advantageous behaviour during formulation or during use, for example during grinding, sieving, emulsifying, dissolving or dispensing; improved storage stability and light stability; advantageous residue formation; improved toxicological or ecotoxicological behaviour; improved properties of the plant, for example better growth, increased harvest yields, a better developed root system, a larger leaf area, greener leaves, stronger shoots, less seed required, lower phytotoxicity, mobilization of the defence system of the plant, good compatibility with plants. Thus, the use of the active compound combinations or compositions according to the invention contributes considerably to keeping young cereal stands healthy, which increases, for example, the winter survival of the cereal seed treated, and also safeguards quality and yield. Moreover, the active compound combinations according to the invention may contribute to enhanced systemic action. Even if the individual compounds of the combination have no sufficient systemic properties, the active compound combinations according to the invention may still have this property. In a similar manner, the active compound combinations according to the invention may result in higher persistency of the fungicidal action.

Accordingly, the present invention provides a combination comprising:

(A) at least one difluoromethyl-nicotinic indanyl carboxamide of the formula (I)

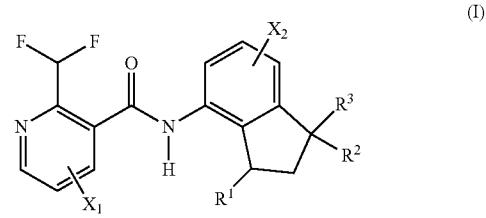

(I)

in which $X_1$, $X_2$ independently represent H, halogen, $C_1$-$C_8$-alkyl, $C_1$-$C_8$-haloalkyl, $C_1$-$C_8$-alkyloxy, $C_1$-$C_8$-alkylsulfanyl, cyano;

$R^1$ represents H, $C_1$-$C_8$-alkyl, $C_1$-$C_8$-haloalkyl, $C_3$-$C_8$-cycloalkyl, $C_3$-$C_8$-halocycloalkyl, $C_1$-$C_4$-alkyl-$C_3$-$C_8$-cycloalkyl; $C_1$-$C_4$-alkyl-$C_3$-$C_8$-halocycloalkyl;

$R^2$, $R^3$ independently represent H, $C_1$-$C_8$-alkyl, $C_1$-$C_8$-haloalkyl, $C_3$-$C_8$-cycloalkyl, $C_3$-$C_8$-halocycloalkyl, $C_1$-$C_4$-alkyl-$C_3$-$C_8$-cycloalkyl, $C_1$-$C_4$-alkyl-$C_3$-$C_8$-halocycloalkyl;

or an agrochemically acceptable salt thereof, and (B) at least one further active compound selected from the group of inhibitors of the respiratory chain at complex I or II.

DETAILED DESCRIPTION OF A PREFERRED EMBODIMENT

Preference is given to combinations comprising at least one difluoromethyl-nicotinic indanyl carboxamide of the formula (I) in which $X_1$ represents H; fluorine in 4-position of the pyridine ring; chlorine in 4-position of the pyridine ring;

$X_2$ represents H, fluorine in 4-position of the phenyl ring; chlorine in 4-position of the phenyl ring;

$R^1$ represents methyl, ethyl, n-propyl, iso-propyl, butyl, iso-butyl, sec-butyl, —$CH_2$-tbutyl;

$R^2$, $R^3$ independently represent methyl, ethyl or isopropyl;

or an agrochemically acceptable salt thereof.

Particular preference is given to combinations comprising at least one compound of the formula (I) selected from the group consisting of

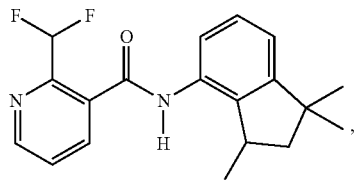
(I-1)

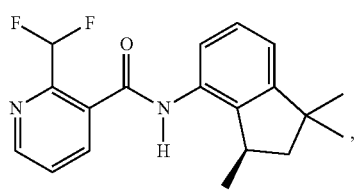
(I-2)

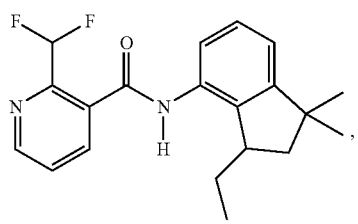
(I-3)

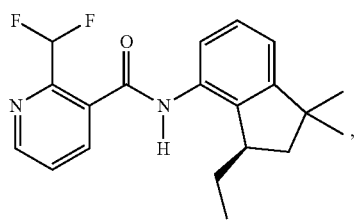
(I-4)

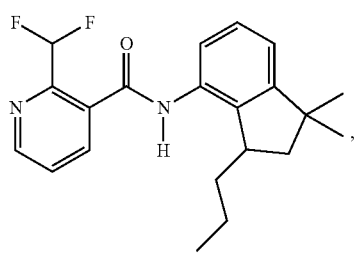
(I-5)

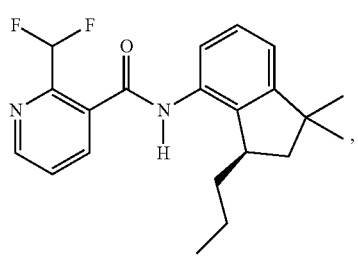
(I-6)

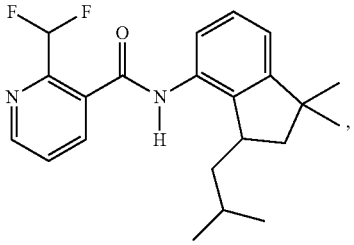
(I-7)

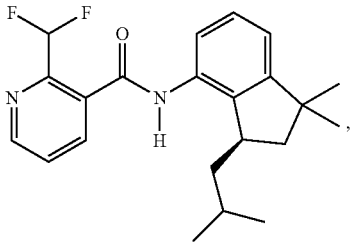
(I-8)

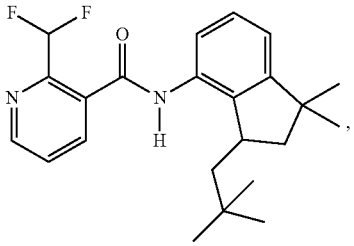
(I-9)

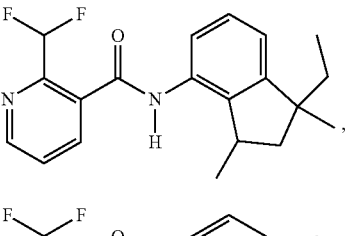
(I-10)

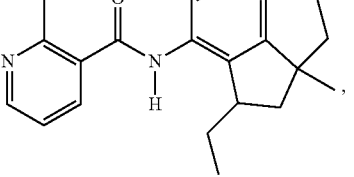
(I-11)

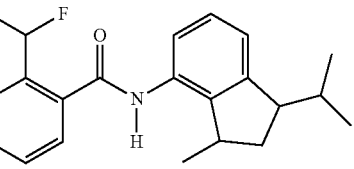
(I-12)

Preference is further given to combinations comprising at least one further active compound (B) selected from the following groups:

(1) Inhibitors of the respiratory chain at complex I or II, for example (1.001) bixafen, (1.002) boscalid, (1.003) carboxin, (1.004) diflumetorim, (1.005) fenfuram, (1.006) fluopyram, (1.007) flutolanil, (1.008) fluxapyroxad, (1.009) furametpyr, (1.010) furmecyclox, (1.011) isopyrazam (mixture of syn-epimeric racemate 1RS,4SR,9RS and anti-epimeric racemate 1RS,4SR,9SR), (1.012) isopyrazam (anti-epimeric racemate 1RS,4SR,9SR), (1.013) isopyrazam (anti-epimeric enantiomer 1R,4S,9S), (1.014) isopyrazam (anti-epimeric enantiomer 1S,4R,9R), (1.015) isopyrazam (syn-epimeric racemate 1RS,4SR,9RS), (1.016) isopyrazam (syn-epimeric enantiomer 1R,4S,9R), (1.017) isopyrazam (syn-epimeric enantiomer 1S,4R,9S), (1.018) mepronil, (1.019) oxycarboxin, (1.020) penflufen, (1.021) penthiopyrad, (1.022) sedaxane, (1.023) thifluzamide, (1.024) 1-methyl-N-[2-(1,1,2,2-tetrafluoroethoxy)phenyl]-3-(trifluoromethyl)-1H-pyrazole-4-carboxamide, (1.025) 3-(difluoromethyl)-1-methyl-N-[2-(1,1,2,2-tetrafluoroethoxy) phenyl]-1H-pyrazole-4-carboxamide, (1.026) 3-(difluoromethyl)-N-[4-fluoro-2-(1,1,2,3,3,3-hexafluoropropoxy)phenyl]-1-methyl-1H-pyrazole-4-carboxamide, (1.027) N-[1-(2,4-dichlorophenyl)-1-methoxypropan-2-yl]-3-(difluoromethyl)-1-methyl-1H-pyrazole-4-carboxamide, (1.028) 5,8-difluoro-N-[2-(2-fluoro-4-{[4-(trifluoromethyl) pyridin-2-yl]oxy}phenyl)ethyl]quinazolin-4-amine, (1.029) benzovindiflupyr, (1.030) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide, (1.031) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (1.032) 3-(difluoromethyl)-1-methyl-N-(1,1,3-trimethyl-2,3-dihydro-1H-inden-4-yl)-1H-pyrazole-4-carboxamide, (1.033) 1,3,5-trimethyl-N-(1,1,3-trimethyl-2,3-dihydro-1H-inden-4-yl)-1H-pyrazole-4-carboxamide, (1.034) 1-methyl-3-(trifluoromethyl)-N-(1,1,3-trimethyl-2,3-dihydro-1H-inden-4-yl)-1H-pyrazole-4-carboxamide, (1.035) 1-methyl-3-(trifluoromethyl)-N-[(3R)-1,1,3-trimethyl-2,3-dihydro-1H-inden-4-yl]-1H-pyrazole-4-carboxamide, (1.036) 1-methyl-3-(trifluoromethyl)-N-[(3S)-1,1,3-trimethyl-2,3-dihydro-1H-inden-4-yl]-1H-pyrazole-4-carboxamide, (1.037) 3-(difluoromethyl)-1-methyl-N-[(3S)-1,1,3-trimethyl-2,3-dihydro-1H-inden-4-yl]-1H-pyrazole-4-carboxamide, (1.038) 3-(difluoromethyl)-1-methyl-N-[(3R)-1,1,3-trimethyl-2,3-dihydro-1H-inden-4-yl]-1H-pyrazole-4-carboxamide, (1.039) 1,3,5-trimethyl-N-[(3R)-1,1,3-trimethyl-2,3-dihydro-1H-inden-4-yl]-1H-pyrazole-4-carboxamide, (1.040) 1,3,5-trimethyl-N-[(3S)-1,1,3-trimethyl-2,3-dihydro-1H-inden-4-yl]-1H-pyrazole-4-carboxamide, (1.041) benodanil, (1.042) 2-chloro-N-(1,1,3-trimethyl-2,3-dihydro-1H-inden-4-yl)pyridine-3-carboxamide, (1.043) Isofetamid, (1.044) 1-methyl-3-(trifluoromethyl)-N-[2'-(trifluoromethyl)biphenyl-2-yl]-1H-pyrazole-4-carboxamide, (1.045) N-(4'-chlorobiphenyl-2-yl)-3-(difluoromethyl)-1-methyl-1H-pyrazole-4-carboxamide, (1.046) N-(2',4'-dichlorobiphenyl-2-yl)-3-(difluoromethyl)-1-methyl-1H-pyrazole-4-carboxamide, (1.047) 3-(difluoromethyl)-1-methyl-N-[4'-(trifluoromethyl)biphenyl-2-yl]-1H-pyrazole-4-carboxamide, (1.048) N-(2',5'-difluorobiphenyl-2-yl)-1-methyl-3-(trifluoromethyl)-1H-pyrazole-4-carboxamide, (1.049) 3-(difluoromethyl)-1-methyl-N-[4'-(prop-1-yn-1-yl) biphenyl-2-yl]-1H-pyrazole-4-carboxamide, (1.050) 5-fluoro-1,3-dimethyl-N-[4'-(prop-1-yn-1-yl)biphenyl-2-yl]-1H-pyrazole-4-carboxamide, (1.051) 2-chloro-N-[4'-(prop-1-yn-1-yl)biphenyl-2-yl]nicotinamide, (1.052) 3-(difluoromethyl)-N-[4'-(3,3-dimethylbut-1-yn-1-yl)biphenyl-2-yl]-1-methyl-1H-pyrazole-4-carboxamide, (1.053) N-[4'-(3,3-dimethylbut-1-yn-1-yl)biphenyl-2-yl]-5-fluoro-1,3-dimethyl-1H-pyrazole-4-carboxamide, (1.054) 3-(difluoromethyl)-N-(4'-ethynylbiphenyl-2-yl)-1-methyl-1H-pyrazole-4-carboxamide, (1.055) N-(4'-ethynylbiphenyl-2-yl)-5-fluoro-1,3-dimethyl-1H-pyrazole-4-carboxamide, (1.056) 2-chloro-N-(4'-ethynylbiphenyl-2-yl) nicotinamide, (1.057) 2-chloro-N-[4'-(3,3-dimethylbut-1-yn-1-yl)biphenyl-2-yl]nicotinamide, (1.058) 4-(difluoromethyl)-2-methyl-N-[4'-(trifluoromethyl)biphenyl-2-yl]-1,3-thiazole-5-carboxamide, (1.059) 5-fluoro-N-[4'-(3-hydroxy-3-methylbut-1-yn-1-yl)biphenyl-2-yl]-1,3-dimethyl-1H-pyrazole-4-carboxamide, (1.060) 2-chloro-N-[4'-(3-hydroxy-3-methylbut-1-yn-1-yl)biphenyl-2-yl] nicotinamide, (1.061) 3-(difluoromethyl)-N-[4'-(3-methoxy-3-methylbut-1-yn-1-yl)biphenyl-2-yl]-1-methyl-1H-pyrazole-4-carboxamide, (1.062) 5-fluoro-N-[4'-(3-methoxy-3-methylbut-1-yn-1-yl)biphenyl-2-yl]-1,3-dimethyl-1H-pyrazole-4-carboxamide, (1.063) 2-chloro-N-[4'-(3-methoxy-3-methylbut-1-yn-1-yl)biphenyl-2-yl] nicotinamide, (1.064) 1,3-dimethyl-N-(1,1,3-trimethyl-2,3-dihydro-1H-inden-4-yl)-1H-pyrazole-4-carboxamide, (1.065) 1,3-dimethyl-N-[(3R)-1,1,3-trimethyl-2,3-dihydro-1H-inden-4-yl]-1H-pyrazole-4-carboxamide, (1.066) 1,3-dimethyl-N-[(3S)-1,1,3-trimethyl-2,3-dihydro-1H-inden-4-yl]-1H-pyrazole-4-carboxamide, (1.067) 3-(difluoromethyl)-N-methoxy-1-methyl-N-[1-(2,4,6-trichlorophenyl)propan-2-yl]-1H-pyrazole-4-carboxamide, (1.068) 3-(difluoromethyl)-N-(7-fluoro-1,1,3-trimethyl-2,3-dihydro-1H-inden-4-yl)-1-methyl-1H-pyrazole-4-carboxamide, (1.069) 3-(difluoromethyl)-N-[(3R)-7-fluoro-1,1,3-trimethyl-2,3-dihydro-1H-inden-4-yl]-1-methyl-1H-pyrazole-4-carboxamide, (1.070) 3-(difluoromethyl)-N-[(3S)-7-fluoro-1,1,3-trimethyl-2,3-dihydro-1H-inden-4-yl]-1-methyl-1H-pyrazole-4-carboxamide, (1.071) Pyraziflumid, (1.072) 2-fluoro-6-(trifluoromethyl)-N-(1,1,3-trimethyl-2,3-dihydro-1H-inden-4-yl)benzamide, (1.073) N-cyclopropyl-3-(difluoromethyl)-5-fluoro-N-(2-isopropylbenzyl)-1-methyl-1H-pyrazole-4-carboxamide, (2.071) N-cyclopropyl-N-(2-cyclopropylbenzyl)-3-(difluoromethyl)-5-fluoro-1-methyl-1H-pyrazole-4-carboxamide, (1.075) N-(2-tert-butylbenzyl)-N-cyclopropyl-3-(difluoromethyl)-5-fluoro-1-methyl-1H-pyrazole-4-carboxamide, (1.076) N-(5-chloro-2-ethylbenzyl)-N-cyclopropyl-3-(difluoromethyl)-5-fluoro-1-methyl-1H-pyrazole-4-carboxamide, (1.077) N-(5-chloro-2-isopropylbenzyl)-N-cyclopropyl-3-(difluoromethyl)-5-fluoro-1-methyl-1H-pyrazole-4-carboxamide, (1.078) N-cyclopropyl-3-(difluoromethyl)-N-(2-ethyl-5-fluorobenzyl)-5-fluoro-1-methyl-1H-pyrazole-4-carboxamide, (1.079) N-cyclopropyl-3-(difluoromethyl)-5-fluoro-N-(5-fluoro-2-isopropylbenzyl)-1-methyl-1H-pyrazole-4-carboxamide, (1.080) N-cyclopropyl-N-(2-cyclopropyl-5-fluorobenzyl)-3-(difluoromethyl)-5-fluoro-1-methyl-1H-pyrazole-4-carboxamide, (1.081) N-(2-cyclopentyl-5-fluorobenzyl)-N-cyclopropyl-3-(difluoromethyl)-5-fluoro-1-methyl-1H-pyrazole-4-carboxamide, (1.082) N-cyclopropyl-3-(difluoromethyl)-5-fluoro-N-(2-fluoro-6-isopropylbenzyl)-1-methyl-1H-pyrazole-4-carboxamide, (1.083) N-cyclopropyl-3-(difluoromethyl)-N-(2-ethyl-5-methylbenzyl)-5-fluoro-1-methyl-1H-pyrazole-4-carboxamide, (1.084) N-cyclopropyl-3-(difluoromethyl)-5-fluoro-N-(2-isopropyl-5-methylbenzyl)-1-methyl-1H-pyrazole-4-carboxamide, (1.085) N-cyclopropyl-N-(2-cyclopropyl-5-methylbenzyl)-3-(difluoromethyl)-5-fluoro-1-methyl-1H-pyrazole-4-carboxamide, (1.086) N-(2-tert-butyl-5-methylbenzyl)-N-cyclopropyl-3-(difluoromethyl)-5-fluoro-1-methyl-1H-pyrazole-4-carboxamide, (1.087) N-[5-chloro-2-(trifluoromethyl)benzyl]-N-cyclopropyl-3-(difluoromethyl)-5-fluoro-1-methyl-1H-pyrazole-4-carboxamide, (1.088) N-cyclopropyl-3-(difluoromethyl)-5-fluoro-1-methyl-N-[5-methyl-2-(trifluoromethyl)benzyl]-1H-pyrazole-4-carboxamide, (1.089) N-[2-chloro-6-(trifluoromethyl)benzyl]-N-cyclopropyl-3-(difluoromethyl)-5-fluoro-1-methyl-1H-pyrazole-4-carboxamide, (1.090) N-[3-chloro-2-fluoro-6-

(trifluoromethyl)benzyl]-N-cyclopropyl-3-(difluoromethyl)-5-fluoro-1-methyl-1H-pyrazole-4-carboxamide, (1.091) N-cyclopropyl-3-(difluoromethyl)-N-(2-ethyl-4,5-dimethylbenzyl)-5-fluoro-1-methyl-1H-pyrazole-4-carboxamide, (1.092) N-cyclopropyl-3-(difluoromethyl)-5-fluoro-N-(2-isopropylbenzyl)-1-methyl-1H-pyrazole-4-carbothioamide.

All named mixing partners of the class (1) can, if their functional groups enable this, optionally form salts with suitable bases or acids.

Particular preference is further given to combinations comprising at least one further active compound (B) selected from the following groups:

(1) Inhibitors of the respiratory chain at complex I or II, for example (1.001) bixafen, (1.002) boscalid, (1.006) fluopyram, (1.008) fluxapyroxad, (1.011) isopyrazam (mixture of syn-epimeric racemate 1RS,4SR,9RS and anti-epimeric racemate 1RS,4SR,9SR), (1.012) isopyrazam (anti-epimeric racemate 1RS,4SR,9SR), (1.013) isopyrazam (anti-epimeric enantiomer 1R,4S,9S), (1.014) isopyrazam (anti-epimeric enantiomer 1S,4R,9R), (1.015) isopyrazam (syn-epimeric racemate 1RS,4SR,9RS), (1.016) isopyrazam (syn-epimeric enantiomer 1R,4S,9R), (1.017) isopyrazam (syn-epimeric enantiomer 1S,4R,9S), (1.020) penflufen, (1.021) penthiopyrad, (1.022) sedaxane, (1.029) benzovindiflupyr, (1.077) N-(5-chloro-2-isopropylbenzyl)-N-cyclopropyl-3-(difluoromethyl)-5-fluoro-1-methyl-1H-pyrazole-4-carboxamide.

In a preferred embodiment this invention is directed to mixtures comprising the compound (I-1) as compound of formula (I) and one component (B), in particular the mixtures (I-1)+(1.001), (I-1)+(1.002), (I-1)+(1.003), (I-1)+(1.004), (I-1)+(1.005), (I-1)+(1.006), (I-1)+(1.007), (I-1)+(1.008), (I-1)+(1.009), (I-1)+(1.010), (I-1)+(1.011), (I-1)+(1.012), (I-1)+(1.013), (I-1)+(1.014), (I-1)+(1.015), (I-1)+(1.016), (I-1)+(1.017), (I-1)+(1.018), (I-1)+(1.019), (I-1)+(1.020), (I-1)+(1.021), (I-1)+(1.022), (I-1)+(1.023), (I-1)+(1.024), (I-1)+(1.025), (I-1)+(1.026), (I-1)+(1.027), (I-1)+(1.028), (I-1)+(1.029), (I-1)+(1.030), (I-1)+(1.031), (I-1)+(1.032), (I-1)+(1.033), (I-1)+(1.034), (I-1)+(1.035), (I-1)+(1.036), (I-1)+(1.037), (I-1)+(1.038), (I-1)+(1.039), (I-1)+(1.040), (I-1)+(1.041), (I-1)+(1.042), (I-1)+(1.043), (I-1)+(1.044), (I-1)+(1.045), (I-1)+(1.046), (I-1)+(1.047), (I-1)+(1.048), (I-1)+(1.049), (I-1)+(1.050), (I-1)+(1.051), (I-1)+(1.052), (I-1)+(1.053), (I-1)+(1.054), (I-1)+(1.055), (I-1)+(1.056), (I-1)+(1.057), (I-1)+(1.058), (I-1)+(1.059), (I-1)+(1.060), (I-1)+(1.061), (I-1)+(1.062), (I-1)+(1.063), (I-1)+(1.064), (I-1)+(1.065), (I-1)+(1.066), (I-1)+(1.067), (I-1)+(1.068), (I-1)+(1.069), (I-1)+(1.070), (I-1)+(1.071), (I-1)+(1.072), (I-1)+(1.073), (I-1)+(1.074), (I-1)+(1.075), (I-1)+(1.076), (I-1)+(1.077), (I-1)+(1.078), (I-1)+(1.079), (I-1)+(1.080), (I-1)+(1.081), (I-1)+(1.082), (I-1)+(1.083), (I-1)+(1.084), (I-1)+(1.085), (I-1)+(1.086), (I-1)+(1.087), (I-1)+(1.088), (I-1)+(1.089), (I-1)+(1.090), (I-1)+(1.091), (I-1)+(1.092).

In a further particularly preferred embodiment this invention is directed to mixtures comprising the compound (I-1) as compound of formula (I) and one component (B), in particular the mixtures (I-1)+(1.001), (I-1)+(1.002), (I-1)+(1.006), (I-1)+(1.008), (I-1)+(1.011), (I-1)+(1.012), (I-1)+(1.013), (I-1)+(1.014) (I-1)+(1.015), (I-1)+(1.016), (I-1)+(1.017), (I-1)+(1.020), (I-1)+(1.021), (I-1)+(1.022), (I-1)+(1.029), (I-1)+(1.077).

In a preferred embodiment this invention is directed to mixtures comprising the compound (I-2) as compound of formula (I) and one component (B), in particular the mixtures (I-2)+(1.001), (I-2)+(1.002), (I-2)+(1.003), (I-2)+(1.004), (I-2)+(1.005), (I-2)+(1.006), (I-2)+(1.007), (I-2)+(1.008), (I-2)+(1.009), (I-2)+(1.010), (I-2)+(1.011), (I-2)+(1.012), (I-2)+(1.013), (I-2)+(1.014), (I-2)+(1.015), (I-2)+(1.016), (I-2)+(1.017), (I-2)+(1.018), (I-2)+(1.019), (I-2)+(1.020), (I-2)+(1.021), (I-2)+(1.022), (I-2)+(1.023), (I-2)+(1.024), (I-2)+(1.025), (I-2)+(1.026), (I-2)+(1.027), (I-2)+(1.028), (I-2)+(1.029), (I-2)+(1.030), (I-2)+(1.031), (I-2)+(1.032), (I-2)+(1.033), (I-2)+(1.034), (I-2)+(1.035), (I-2)+(1.036), (I-2)+(1.037), (I-2)+(1.038), (I-2)+(1.039), (I-2)+(1.040), (I-2)+(1.041), (I-2)+(1.042), (I-2)+(1.043), (I-2)+(1.044), (I-2)+(1.045), (I-2)+(1.046), (I-2)+(1.047), (I-2)+(1.048), (I-2)+(1.049), (I-2)+(1.050), (I-2)+(1.051), (I-2)+(1.052), (I-2)+(1.053), (I-2)+(1.054), (I-2)+(1.055), (I-2)+(1.056), (I-2)+(1.057), (I-2)+(1.058), (I-2)+(1.059), (I-2)+(1.060), (I-2)+(1.061), (I-2)+(1.062), (I-2)+(1.063), (I-2)+(1.064), (I-2)+(1.065), (I-2)+(1.066), (I-2)+(1.067), (I-2)+(1.068), (I-2)+(1.069), (I-2)+(1.070), (I-2)+(1.071), (I-2)+(1.072), (I-2)+(1.073), (I-2)+(1.074), (I-2)+(1.075), (I-2)+(1.076), (I-2)+(1.077), (I-2)+(1.078), (I-2)+(1.079), (I-2)+(1.080), (I-2)+(1.081), (I-2)+(1.082), (I-2)+(1.083), (I-2)+(1.084), (I-2)+(1.085), (I-2)+(1.086), (I-2)+(1.087), (I-2)+(1.088), (I-2)+(1.089), (I-2)+(1.090), (I-2)+(1.091), (I-2)+(1.092).

In a further particularly preferred embodiment this invention is directed to mixtures comprising the compound (I-2) as compound of formula (I) and one component (B), in particular the mixtures (I-2)+(1.001), (I-2)+(1.002), (I-2)+(1.006), (I-2)+(1.008), (I-2)+(1.011), (I-2)+(1.012), (I-2)+(1.013), (I-2)+(1.014) (I-2)+(1.015), (I-2)+(1.016), (I-2)+(1.017), (I-2)+(1.020), (I-2)+(1.021), (I-2)+(1.022), (I-2)+(1.029), (I-2)+(1.077).

In a preferred embodiment this invention is directed to mixtures comprising the compound (I-3) as compound of formula (I) and one component (B), in particular the mixtures (I-3)+(1.001), (I-3)+(1.002), (I-3)+(1.003), (I-3)+(1.004), (I-3)+(1.005), (I-3)+(1.006), (I-3)+(1.007), (I-3)+(1.008), (I-3)+(1.009), (I-3)+(1.010), (I-3)+(1.011), (I-3)+(1.012), (I-3)+(1.013), (I-3)+(1.014), (I-3)+(1.015), (I-3)+(1.016), (I-3)+(1.017), (I-3)+(1.018), (I-3)+(1.019), (I-3)+(1.020), (I-3)+(1.021), (I-3)+(1.022), (I-3)+(1.023), (I-3)+(1.024), (I-3)+(1.025), (I-3)+(1.026), (I-3)+(1.027), (I-3)+(1.028), (I-3)+(1.029), (I-3)+(1.030), (I-3)+(1.031), (I-3)+(1.032), (I-3)+(1.033), (I-3)+(1.034), (I-3)+(1.035), (I-3)+(1.036), (I-3)+(1.037), (I-3)+(1.038), (I-3)+(1.039), (I-3)+(1.040), (I-3)+(1.041), (I-3)+(1.042), (I-3)+(1.043), (I-3)+(1.044), (I-3)+(1.045), (I-3)+(1.046), (I-3)+(1.047), (I-3)+(1.048), (I-3)+(1.049), (I-3)+(1.050), (I-3)+(1.051), (I-3)+(1.052), (I-3)+(1.053), (I-3)+(1.054), (I-3)+(1.055), (I-3)+(1.056), (I-3)+(1.057), (I-3)+(1.058), (I-3)+(1.059), (I-3)+(1.060), (I-3)+(1.061), (I-3)+(1.062), (I-3)+(1.063), (I-3)+(1.064), (I-3)+(1.065), (I-3)+(1.066), (I-3)+(1.067), (I-3)+(1.068), (I-3)+(1.069), (I-3)+(1.070), (I-3)+(1.071), (I-3)+(1.072), (I-3)+(1.073), (I-3)+(1.074), (I-3)+(1.075), (I-3)+(1.076), (I-3)+(1.077), (I-3)+(1.078), (I-3)+(1.079), (I-3)+(1.080), (I-3)+(1.081), (I-3)+(1.082), (I-3)+(1.083), (I-3)+(1.084), (I-3)+(1.085), (I-3)+(1.086), (I-3)+(1.087), (I-3)+(1.088), (I-3)+(1.089), (I-3)+(1.090), (I-3)+(1.091), (I-3)+(1.092).

In a further particularly preferred embodiment this invention is directed to mixtures comprising the compound (I-3) as compound of formula (I) and one component (B), in particular the mixtures (I-3)+(1.001), (I-3)+(1.002), (I-3)+(1.006), (I-3)+(1.008), (I-3)+(1.011), (I-3)+(1.012), (I-3)+(1.013), (I-3)+(1.014) (I-3)+(1.015), (I-3)+(1.016), (I-3)+(1.017), (I-3)+(1.020), (I-3)+(1.021), (I-3)+(1.022), (I-3)+(1.029), (I-3)+(1.077).

In a preferred embodiment this invention is directed to mixtures comprising the compound (I-4) as compound of formula (I) and one component (B), in particular the mixtures (I-4)+(1.001), (I-4)+(1.002), (I-4)+(1.003), (I-4)+(1.004), (I-4)+(1.005), (I-4)+(1.006), (I-4)+(1.007), (I-4)+(1.008), (I-4)+(1.009), (I-4)+(1.010), (I-4)+(1.011), (I-4)+(1.012), (I-4)+(1.013), (I-4)+(1.014), (I-4)+(1.015), (I-4)+(1.016), (I-4)+(1.017), (I-4)+(1.018), (I-4)+(1.019), (I-4)+(1.020), (I-4)+(1.021), (I-4)+(1.022), (I-4)+(1.023), (I-4)+(1.024), (I-4)+(1.025), (I-4)+(1.026), (I-4)+(1.027), (I-4)+(1.028), (I-4)+(1.029), (I-4)+(1.030), (I-4)+(1.031), (I-4)+(1.032), (I-4)+(1.033), (I-4)+(1.034), (I-4)+(1.035), (I-4)+(1.036), (I-4)+(1.037), (I-4)+(1.038), (I-4)+(1.039), (I-4)+(1.040), (I-4)+(1.041), (I-4)+(1.042), (I-4)+(1.043), (I-4)+(1.044), (I-4)+(1.045), (I-4)+(1.046), (I-4)+(1.047), (I-4)+(1.048), (I-4)+(1.049), (I-4)+(1.050), (I-4)+(1.051), (I-4)+(1.052), (I-4)+(1.053), (I-4)+(1.054), (I-4)+(1.055), (I-4)+(1.056), (I-4)+(1.057), (I-4)+(1.058), (I-4)+(1.059), (I-4)+(1.060), (I-4)+(1.061), (I-4)+(1.062), (I-4)+(1.063), (I-4)+(1.064), (I-4)+(1.065), (I-4)+(1.066), (I-4)+(1.067), (I-4)+(1.068), (I-4)+(1.069), (I-4)+(1.070), (I-4)+(1.071), (I-4)+(1.072), (I-4)+(1.073), (I-4)+(1.074), (I-4)+(1.075), (I-4)+(1.076), (I-4)+(1.077), (I-4)+(1.078), (I-4)+(1.079), (I-4)+(1.080), (I-4)+(1.081), (I-4)+(1.082), (I-4)+(1.083), (I-4)+(1.084), (I-4)+(1.085), (I-4)+(1.086), (I-4)+(1.087), (I-4)+(1.088), (I-4)+(1.089), (I-4)+(1.090), (I-4)+(1.091), (I-4)+(1.092).

In a further particularly preferred embodiment this invention is directed to mixtures comprising the compound (I-4) as compound of formula (I) and one component (B), in particular the mixtures (I-4)+(1.001), (I-4)+(1.002), (I-4)+(1.006), (I-4)+(1.008), (I-4)+(1.011), (I-4)+(1.012), (I-4)+(1.013), (I-4)+(1.014) (I-4)+(1.015), (I-4)+(1.016), (I-4)+(1.017), (I-4)+(1.020), (I-4)+(1.021), (I-4)+(1.022), (I-4)+(1.029), (I-4)+(1.077).

In a preferred embodiment this invention is directed to mixtures comprising the compound (I-5) as compound of formula (I) and one component (B), in particular the mixtures (I-5)+(1.001), (I-5)+(1.002), (I-5)+(1.003), (I-5)+(1.004), (I-5)+(1.005), (I-5)+(1.006), (I-5)+(1.007), (I-5)+(1.008), (I-5)+(1.009), (I-5)+(1.010), (I-5)+(1.011), (I-5)+(1.012), (I-5)+(1.013), (I-5)+(1.014), (I-5)+(1.015), (I-5)+(1.016), (I-5)+(1.017), (I-5)+(1.018), (I-5)+(1.019), (I-5)+(1.020), (I-5)+(1.021), (I-5)+(1.022), (I-5)+(1.023), (I-5)+(1.024), (I-5)+(1.025), (I-5)+(1.026), (I-5)+(1.027), (I-5)+(1.028), (I-5)+(1.029), (I-5)+(1.030), (I-5)+(1.031), (I-5)+(1.032), (I-5)+(1.033), (I-5)+(1.034), (I-5)+(1.035), (I-5)+(1.036), (I-5)+(1.037), (I-5)+(1.038), (I-5)+(1.039), (I-5)+(1.040), (I-5)+(1.041), (I-5)+(1.042), (I-5)+(1.043), (I-5)+(1.044), (I-5)+(1.045), (I-5)+(1.046), (I-5)+(1.047), (I-5)+(1.048), (I-5)+(1.049), (I-5)+(1.050), (I-5)+(1.051), (I-5)+(1.052), (I-5)+(1.053), (I-5)+(1.054), (I-5)+(1.055), (I-5)+(1.056), (I-5)+(1.057), (I-5)+(1.058), (I-5)+(1.059), (I-5)+(1.060), (I-5)+(1.061), (I-5)+(1.062), (I-5)+(1.063), (I-5)+(1.064), (I-5)+(1.065), (I-5)+(1.066), (I-5)+(1.067), (I-5)+(1.068), (I-5)+(1.069), (I-5)+(1.070), (I-5)+(1.071), (I-5)+(1.072), (I-5)+(1.073), (I-5)+(1.074), (I-5)+(1.075), (I-5)+(1.076), (I-5)+(1.077), (I-5)+(1.078), (I-5)+(1.079), (I-5)+(1.080), (I-5)+(1.081), (I-5)+(1.082), (I-5)+(1.083), (I-5)+(1.084), (I-5)+(1.085), (I-5)+(1.086), (I-5)+(1.087), (I-5)+(1.088), (I-5)+(1.089), (I-5)+(1.090), (I-5)+(1.091), (I-5)+(1.092).

In a further particularly preferred embodiment this invention is directed to mixtures comprising the compound (I-5) as compound of formula (I) and one component (B), in particular the mixtures (I-5)+(1.001), (I-5)+(1.002), (I-5)+(1.006), (I-5)+(1.008), (I-5)+(1.011), (I-5)+(1.012), (I-5)+(1.013), (I-5)+(1.014) (I-5)+(1.015), (I-5)+(1.016), (I-5)+(1.017), (I-5)+(1.020), (I-5)+(1.021), (I-5)+(1.022), (I-5)+(1.029), (I-5)+(1.077).

In a preferred embodiment this invention is directed to mixtures comprising the compound (I-6) as compound of formula (I) and one component (B), in particular the mixtures (I-6)+(1.001), (I-6)+(1.002), (I-6)+(1.003), (I-6)+(1.004), (I-6)+(1.005), (I-6)+(1.006), (I-6)+(1.007), (I-6)+(1.008), (I-6)+(1.009), (I-6)+(1.010), (I-6)+(1.011), (I-6)+(1.012), (I-6)+(1.013), (I-6)+(1.014), (I-6)+(1.015), (I-6)+(1.016), (I-6)+(1.017), (I-6)+(1.018), (I-6)+(1.019), (I-6)+(1.020), (I-6)+(1.021), (I-6)+(1.022), (I-6)+(1.023), (I-6)+(1.024), (I-6)+(1.025), (I-6)+(1.026), (I-6)+(1.027), (I-6)+(1.028), (I-6)+(1.029), (I-6)+(1.030), (I-6)+(1.031), (I-6)+(1.032), (I-6)+(1.033), (I-6)+(1.034), (I-6)+(1.035), (I-6)+(1.036), (I-6)+(1.037), (I-6)+(1.038), (I-6)+(1.039), (I-6)+(1.040), (I-6)+(1.041), (I-6)+(1.042), (I-6)+(1.043), (I-6)+(1.044), (I-6)+(1.045), (I-6)+(1.046), (I-6)+(1.047), (I-6)+(1.048), (I-6)+(1.049), (I-6)+(1.050), (I-6)+(1.051), (I-6)+(1.052), (I-6)+(1.053), (I-6)+(1.054), (I-6)+(1.055), (I-6)+(1.056), (I-6)+(1.057), (I-6)+(1.058), (I-6)+(1.059), (I-6)+(1.060), (I-6)+(1.061), (I-6)+(1.062), (I-6)+(1.063), (I-6)+(1.064), (I-6)+(1.065), (I-6)+(1.066), (I-6)+(1.067), (I-6)+(1.068), (I-6)+(1.069), (I-6)+(1.070), (I-6)+(1.071), (I-6)+(1.072), (I-6)+(1.073), (I-6)+(1.074), (I-6)+(1.075), (I-6)+(1.076), (I-6)+(1.077), (I-6)+(1.078), (I-6)+(1.079), (I-6)+(1.080), (I-6)+(1.081), (I-6)+(1.082), (I-6)+(1.083), (I-6)+(1.084), (I-6)+(1.085), (I-6)+(1.086), (I-6)+(1.087), (I-6)+(1.088), (I-6)+(1.089), (I-6)+(1.090), (I-6)+(1.091), (I-6)+(1.092).

In a further particularly preferred embodiment this invention is directed to mixtures comprising the compound (I-6) as compound of formula (I) and one component (B), in particular the mixtures (I-6)+(1.001), (I-6)+(1.002), (I-6)+(1.006), (I-6)+(1.008), (I-6)+(1.011), (I-6)+(1.012), (I-6)+(1.013), (I-6)+(1.014) (I-6)+(1.015), (I-6)+(1.016), (I-6)+(1.017), (I-6)+(1.020), (I-6)+(1.021), (I-6)+(1.022), (I-6)+(1.029), (I-6)+(1.077).

In a preferred embodiment this invention is directed to mixtures comprising the compound (I-7) as compound of formula (I) and one component (B), in particular the mixtures (I-7)+(1.001), (I-7)+(1.002), (I-7)+(1.003), (I-7)+(1.004), (I-7)+(1.005), (I-7)+(1.006), (I-7)+(1.007), (I-7)+(1.008), (I-7)+(1.009), (I-7)+(1.010), (I-7)+(1.011), (I-7)+(1.012), (I-7)+(1.013), (I-7)+(1.014), (I-7)+(1.015), (I-7)+(1.016), (I-7)+(1.017), (I-7)+(1.018), (I-7)+(1.019), (I-7)+(1.020), (I-7)+(1.021), (I-7)+(1.022), (I-7)+(1.023), (I-7)+(1.024), (I-7)+(1.025), (I-7)+(1.026), (I-7)+(1.027), (I-7)+(1.028), (I-7)+(1.029), (I-7)+(1.030), (I-7)+(1.031), (I-7)+(1.032), (I-7)+(1.033), (I-7)+(1.034), (I-7)+(1.035), (I-7)+(1.036), (I-7)+(1.037), (I-7)+(1.038), (I-7)+(1.039), (I-7)+(1.040), (I-7)+(1.041), (I-7)+(1.042), (I-7)+(1.043), (I-7)+(1.044), (I-7)+(1.045), (I-7)+(1.046), (I-7)+(1.047), (I-7)+(1.048), (I-7)+(1.049), (I-7)+(1.050), (I-7)+(1.051), (I-7)+(1.052), (I-7)+(1.053), (I-7)+(1.054), (I-7)+(1.055), (I-7)+(1.056), (I-7)+(1.057), (I-7)+(1.058), (I-7)+(1.059), (I-7)+(1.060), (I-7)+(1.061), (I-7)+(1.062), (I-7)+(1.063), (I-7)+(1.064), (I-7)+(1.065), (I-7)+(1.066), (I-7)+(1.067), (I-7)+(1.068), (I-7)+(1.069), (I-7)+(1.070), (I-7)+(1.071), (I-7)+(1.072), (I-7)+(1.073), (I-7)+(1.074), (I-7)+(1.075), (I-7)+(1.076), (I-7)+(1.077), (I-7)+(1.078), (I-7)+(1.079), (I-7)+(1.080), (I-7)+(1.081), (I-7)+(1.082), (I-7)+(1.083), (I-7)+(1.084), (I-7)+(1.085), (I-7)+(1.086), (I-7)+(1.087), (I-7)+(1.088), (I-7)+(1.089), (I-7)+(1.090), (I-7)+(1.091), (I-7)+(1.092).

In a further particularly preferred embodiment this invention is directed to mixtures comprising the compound (I-7)

as compound of formula (I) and one component (B), in particular the mixtures (I-7)+(1.001), (I-7)+(1.002), (I-7)+(1.006), (I-7)+(1.008), (I-7)+(1.011), (I-7)+(1.012), (I-7)+(1.013), (I-7)+(1.014) (I-7)+(1.015), (I-7)+(1.016), (I-7)+(1.017), (I-7)+(1.020), (I-7)+(1.021), (I-7)+(1.022), (I-7)+(1.029), (I-7)+(1.077).

In a preferred embodiment this invention is directed to mixtures comprising the compound (I-8) as compound of formula (I) and one component (B), in particular the mixtures (I-8)+(1.001), (I-8)+(1.002), (I-8)+(1.003), (I-8)+(1.004), (I-8)+(1.005), (I-8)+(1.006), (I-8)+(1.007), (I-8)+(1.008), (I-8)+(1.009), (I-8)+(1.010), (I-8)+(1.011), (I-8)+(1.012), (I-8)+(1.013), (I-8)+(1.014), (I-8)+(1.015), (I-8)+(1.016), (I-8)+(1.017), (I-8)+(1.018), (I-8)+(1.019), (I-8)+(1.020), (I-8)+(1.021), (I-8)+(1.022), (I-8)+(1.023), (I-8)+(1.024), (I-8)+(1.025), (I-8)+(1.026), (I-8)+(1.027), (I-8)+(1.028), (I-8)+(1.029), (I-8)+(1.030), (I-8)+(1.031), (I-8)+(1.032), (I-8)+(1.033), (I-8)+(1.034), (I-8)+(1.035), (I-8)+(1.036), (I-8)+(1.037), (I-8)+(1.038), (I-8)+(1.039), (I-8)+(1.040), (I-8)+(1.041), (I-8)+(1.042), (I-8)+(1.043), (I-8)+(1.044), (I-8)+(1.045), (I-8)+(1.046), (I-8)+(1.047), (I-8)+(1.048), (I-8)+(1.049), (I-8)+(1.050), (I-8)+(1.051), (I-8)+(1.052), (I-8)+(1.053), (I-8)+(1.054), (I-8)+(1.055), (I-8)+(1.056), (I-8)+(1.057), (I-8)+(1.058), (I-8)+(1.059), (I-8)+(1.060), (I-8)+(1.061), (I-8)+(1.062), (I-8)+(1.063), (I-8)+(1.064), (I-8)+(1.065), (I-8)+(1.066), (I-8)+(1.067), (I-8)+(1.068), (I-8)+(1.069), (I-8)+(1.070), (I-8)+(1.071), (I-8)+(1.072), (I-8)+(1.073), (I-8)+(1.074), (I-8)+(1.075), (I-8)+(1.076), (I-8)+(1.077), (I-8)+(1.078), (I-8)+(1.079), (I-8)+(1.080), (I-8)+(1.081), (I-8)+(1.082), (I-8)+(1.083), (I-8)+(1.084), (I-8)+(1.085), (I-8)+(1.086), (I-8)+(1.087), (I-8)+(1.088), (I-8)+(1.089), (I-8)+(1.090), (I-8)+(1.091), (I-8)+(1.092).

In a further particularly preferred embodiment this invention is directed to mixtures comprising the compound (I-8) as compound of formula (I) and one component (B), in particular the mixtures (I-8)+(1.001), (I-8)+(1.002), (I-8)+(1.006), (I-8)+(1.008), (I-8)+(1.011), (I-8)+(1.012), (I-8)+(1.013), (I-8)+(1.014) (I-8)+(1.015), (I-8)+(1.016), (I-8)+(1.017), (I-8)+(1.020), (I-8)+(1.021), (I-8)+(1.022), (I-8)+(1.029), (I-8)+(1.077).

In a preferred embodiment this invention is directed to mixtures comprising the compound (I-9) as compound of formula (I) and one component (B), in particular the mixtures (I-9)+(1.001), (I-9)+(1.002), (I-9)+(1.003), (I-9)+(1.004), (I-9)+(1.005), (I-9)+(1.006), (I-9)+(1.007), (I-9)+(1.008), (I-9)+(1.009), (I-9)+(1.010), (I-9)+(1.011), (I-9)+(1.012), (I-9)+(1.013), (I-9)+(1.014), (I-9)+(1.015), (I-9)+(1.016), (I-9)+(1.017), (I-9)+(1.018), (I-9)+(1.019), (I-9)+(1.020), (I-9)+(1.021), (I-9)+(1.022), (I-9)+(1.023), (I-9)+(1.024), (I-9)+(1.025), (I-9)+(1.026), (I-9)+(1.027), (I-9)+(1.028), (I-9)+(1.029), (I-9)+(1.030), (I-9)+(1.031), (I-9)+(1.032), (I-9)+(1.033), (I-9)+(1.034), (I-9)+(1.035), (I-9)+(1.036), (I-9)+(1.037), (I-9)+(1.038), (I-9)+(1.039), (I-9)+(1.040), (I-9)+(1.041), (I-9)+(1.042), (I-9)+(1.043), (I-9)+(1.044), (I-9)+(1.045), (I-9)+(1.046), (I-9)+(1.047), (I-9)+(1.048), (I-9)+(1.049), (I-9)+(1.050), (I-9)+(1.051), (I-9)+(1.052), (I-9)+(1.053), (I-9)+(1.054), (I-9)+(1.055), (I-9)+(1.056), (I-9)+(1.057), (I-9)+(1.058), (I-9)+(1.059), (I-9)+(1.060), (I-9)+(1.061), (I-9)+(1.062), (I-9)+(1.063), (I-9)+(1.064), (I-9)+(1.065), (I-9)+(1.066), (I-9)+(1.067), (I-9)+(1.068), (I-9)+(1.069), (I-9)+(1.070), (I-9)+(1.071), (I-9)+(1.072), (I-9)+(1.073), (I-9)+(1.074), (I-9)+(1.075), (I-9)+(1.076), (I-9)+(1.077), (I-9)+(1.078), (I-9)+(1.079), (I-9)+(1.080), (I-9)+(1.081), (I-9)+(1.082), (I-9)+(1.083), (I-9)+(1.084), (I-9)+(1.085), (I-9)+(1.086), (I-9)+(1.087), (I-9)+(1.088), (I-9)+(1.089), (I-9)+(1.090), (I-9)+(1.091), (I-9)+(1.092).

In a further particularly preferred embodiment this invention is directed to mixtures comprising the compound (I-9) as compound of formula (I) and one component (B), in particular the mixtures (I-9)+(1.001), (I-9)+(1.002), (I-9)+(1.006), (I-9)+(1.008), (I-9)+(1.011), (I-9)+(1.012), (I-9)+(1.013), (I-9)+(1.014) (I-9)+(1.015), (I-9)+(1.016), (I-9)+(1.017), (I-9)+(1.020), (I-9)+(1.021), (I-9)+(1.022), (I-9)+(1.029), (I-9)+(1.077).

In a preferred embodiment this invention is directed to mixtures comprising the compound (I-10) as compound of formula (I) and one component (B), in particular the mixtures (I-10)+(1.001), (I-10)+(1.002), (I-10)+(1.003), (I-10)+(1.004), (I-10)+(1.005), (I-10)+(1.006), (I-10)+(1.007), (I-10)+(1.008), (I-10)+(1.009), (I-10)+(1.010), (I-10)+(1.011), (I-10)+(1.012), (I-10)+(1.013), (I-10)+(1.014), (I-10)+(1.015), (I-10)+(1.016), (I-10)+(1.017), (I-10)+(1.018), (I-10)+(1.019), (I-10)+(1.020), (I-10)+(1.021), (I-10)+(1.022), (I-10)+(1.023), (I-10)+(1.024), (I-10)+(1.025), (I-10)+(1.026), (I-10)+(1.027), (I-10)+(1.028), (I-10)+(1.029), (I-10)+(1.030), (I-10)+(1.031), (I-10)+(1.032), (I-10)+(1.033), (I-10)+(1.034), (I-10)+(1.035), (I-10)+(1.036), (I-10)+(1.037), (I-10)+(1.038), (I-10)+(1.039), (I-10)+(1.040), (I-10)+(1.041), (I-10)+(1.042), (I-10)+(1.043), (I-10)+(1.044), (I-10)+(1.045), (I-10)+(1.046), (I-10)+(1.047), (I-10)+(1.048), (I-10)+(1.049), (I-10)+(1.050), (I-10)+(1.051), (I-10)+(1.052), (I-10)+(1.053), (I-10)+(1.054), (I-10)+(1.055), (I-10)+(1.056), (I-10)+(1.057), (I-10)+(1.058), (I-10)+(1.059), (I-10)+(1.060), (I-10)+(1.061), (I-10)+(1.062), (I-10)+(1.063), (I-10)+(1.064), (I-10)+(1.065), (I-10)+(1.066), (I-10)+(1.067), (I-10)+(1.068), (I-10)+(1.069), (I-10)+(1.070), (I-10)+(1.071), (I-10)+(1.072), (I-10)+(1.073), (I-10)+(1.074), (I-10)+(1.075), (I-10)+(1.076), (I-10)+(1.077), (I-10)+(1.078), (I-10)+(1.079), (I-10)+(1.080), (I-10)+(1.081), (I-10)+(1.082), (I-10)+(1.083), (I-10)+(1.084), (I-10)+(1.085), (I-10)+(1.086), (I-10)+(1.087), (I-10)+(1.088), (I-10)+(1.089), (I-10)+(1.090), (I-10)+(1.091), (I-10)+(1.092).

In a further particularly preferred embodiment this invention is directed to mixtures comprising the compound (I-10) as compound of formula (I) and one component (B), in particular the mixtures (I-10)+(1.001), (I-10)+(1.002), (I-10)+(1.006), (I-10)+(1.008), (I-10)+(1.011), (I-10)+(1.012), (I-10)+(1.013), (I-10)+(1.014) (I-10)+(1.015), (I-10)+(1.016), (I-10)+(1.017), (I-10)+(1.020), (I-10)+(1.021), (I-10)+(1.022), (I-10)+(1.029), (I-10)+(1.077).

In a preferred embodiment this invention is directed to mixtures comprising the compound (I-11) as compound of formula (I) and one component (B), in particular the mixtures (I-11)+(1.001), (I-11)+(1.002), (I-11)+(1.003), (I-11)+(1.004), (I-11)+(1.005), (I-11)+(1.006), (I-11)+(1.007), (I-11)+(1.008), (I-11)+(1.009), (I-11)+(1.010), (I-11)+(1.011), (I-11)+(1.012), (I-11)+(1.013), (I-11)+(1.014), (I-11)+(1.015), (I-11)+(1.016), (I-11)+(1.017), (I-11)+(0.018), (I-11)+(1.019), (I-11)+(1.020), (I-11)+(1.021), (I-11)+(1.022), (I-11)+(1.023), (I-11)+(1.024), (I-11)+(1.025), (I-11)+(1.026), (I-11)+(1.027), (I-11)+(1.028), (I-11)+(1.029), (I-11)+(1.030), (I-11)+(1.031), (I-11)+(1.032), (I-11)+(1.033), (I-11)+(1.034), (I-11)+(1.035), (I-11)+(1.036), (I-11)+(1.037), (I-11)+(1.038), (I-11)+(1.039), (I-11)+(1.040), (I-11)+(1.041), (I-11)+(1.042), (I-11)+(1.043), (I-11)+(1.044), (I-11)+(1.045), (I-11)+(1.046), (I-11)+(1.047), (I-11)+(1.048), (I-11)+(1.049), (I-11)+(1.050), (I-11)+(1.051), (I-11)+(1.052), (I-11)+

(1.053), (I-11)+(1.054), (I-11)+(1.055), (I-11)+(1.056), (I-11)+(1.057), (I-11)+(1.058), (I-11)+(1.059), (I-11)+(1.060), (I-11)+(1.061), (I-11)+(1.062), (I-11)+(1.063), (I-11)+(1.064), (I-11)+(1.065), (I-11)+(1.066), (I-11)+(1.067), (I-11)+(1.068), (I-11)+(1.069), (I-11)+(1.070), (I-11)+(1.071), (I-11)+(1.072), (I-11)+(1.073), (I-11)+(1.074), (I-11)+(1.075), (I-11)+(1.076), (I-11)+(1.077), (I-11)+(1.078), (I-11)+(1.079), (I-11)+(1.080), (I-11)+(1.081), (I-11)+(1.082), (I-11)+(1.083), (I-11)+(1.084), (I-11)+(1.085), (I-11)+(1.086), (I-11)+(1.087), (I-11)+(1.088), (I-11)+(1.089), (I-11)+(1.090), (I-11)+(1.091), (I-11)+(1.092).

In a further particularly preferred embodiment this invention is directed to mixtures comprising the compound (I-11) as compound of formula (I) and one component (B), in particular the mixtures (I-11)+(1.001), (I-11)+(1.002), (I-11)+(1.006), (I-11)+(1.008), (I-11)+(1.011), (I-11)+(1.012), (I-11)+(1.013), (I-11)+(1.014) (I-11)+(1.015), (I-11)+(1.016), (I-11)+(1.017), (I-11)+(1.020), (I-11)+(1.021), (I-11)+(1.022), (I-11)+(1.029), (I-11)+(1.077).

In a preferred embodiment this invention is directed to mixtures comprising the compound (I-12) as compound of formula (I) and one component (B), in particular the mixtures (I-12)+(1.001), (I-12)+(1.002), (I-12)+(1.003), (I-12)+(1.004), (I-12)+(1.005), (I-12)+(1.006), (I-12)+(1.007), (I-12)+(1.008), (I-12)+(1.009), (I-12)+(1.010), (I-12)+(1.011), (I-12)+(1.012), (I-12)+(1.013), (I-12)+(1.014), (I-12)+(1.015), (I-12)+(1.016), (I-12)+(1.017), (I-12)+(1.018), (I-12)+(1.019), (I-12)+(1.020), (I-12)+(1.021), (I-12)+(1.022), (I-12)+(1.023), (I-12)+(1.024), (I-12)+(1.025), (I-12)+(1.026), (I-12)+(1.027), (I-12)+(1.028), (I-12)+(1.029), (I-12)+(1.030), (I-12)+(1.031), (I-12)+(1.032), (I-12)+(1.033), (I-12)+(1.034), (I-12)+(1.035), (I-12)+(1.036), (I-12)+(1.037), (I-12)+(1.038), (I-12)+(1.039), (I-12)+(1.040), (I-12)+(1.041), (I-12)+(1.042), (I-12)+(1.043), (I-12)+(1.044), (I-12)+(1.045), (I-12)+(1.046), (I-12)+(1.047), (I-12)+(1.048), (I-12)+(1.049), (I-12)+(1.050), (I-12)+(1.051), (I-12)+(1.052), (I-12)+(1.053), (I-12)+(1.054), (I-12)+(1.055), (I-12)+(1.056), (I-12)+(1.057), (I-12)+(1.058), (I-12)+(1.059), (I-12)+(1.060), (I-12)+(1.061), (I-12)+(1.062), (I-12)+(1.063), (I-12)+(1.064), (I-12)+(1.065), (I-12)+(1.066), (I-12)+(1.067), (I-12)+(1.068), (I-12)+(1.069), (I-12)+(1.070), (I-12)+(1.071), (I-12)+(1.072), (I-12)+(1.073), (I-12)+(1.074), (I-12)+(1.075), (I-12)+(1.076), (I-12)+(1.077), (I-12)+(1.078), (I-12)+(1.079), (I-12)+(1.080), (I-12)+(1.081), (I-12)+(1.082), (I-12)+(1.083), (I-12)+(1.084), (I-12)+(1.085), (I-12)+(1.086), (I-12)+(1.087), (I-12)+(1.088), (I-12)+(1.089), (I-12)+(1.090), (I-12)+(1.091), (I-12)+(1.092).

In a further particularly preferred embodiment this invention is directed to mixtures comprising the compound (I-12) as compound of formula (I) and one component (B), in particular the mixtures (I-12)+(1.001), (I-12)+(1.002), (I-12)+(1.006), (I-12)+(1.008), (I-12)+(1.011), (I-12)+(1.012), (I-12)+(1.013), (I-12)+(1.014) (I-12)+(1.015), (I-12)+(1.016), (I-12)+(1.017), (I-12)+(1.020), (I-12)+(1.021), (I-12)+(1.022), (I-12)+(1.029), (I-12)+(1.077).

If the active compounds in the active compound combinations according to the invention are present in certain weight ratios, the synergistic effect is particularly pronounced. However, the weight ratios of the active compounds in the active compound combinations can be varied within a relatively wide range.

In the combinations according to the invention the compounds (A) and (B) are present in a synergistically effective weight ratio of A:B in a range of 500:1 to 1:500, preferably in a weight ratio of 200:1 to 1:200, most preferably in a weight ratio of 100:1 to 1:100. Further ratios of A:B which can be used according to the present invention with increasing preference in the order given are: 250:1 to 1:250, 220:1 to 1:220, 200:1 to 1:200, 170:1 to 1:170, 140:1 to 1:140, 120:1 to 1:120, 100:1 to 1:100, 95:1 to 1:95, 90:1 to 1:90, 85:1 to 1:85, 80:1 to 1:80, 75:1 to 1:75, 70:1 to 1:70, 65:1 to 1:65, 60:1 to 1:60, 55:1 to 1:55, 45:1 to 1:45, 40:1 to 1:40, 35:1 to 1:35, 30:1 to 1:30, 25:1 to 1:25, 15:1 to 1:15, 10:1 to 1:10, 5:1 to 1:5, 4:1 to 1:4, 3:1 to 1:3, 2:1 to 1:2.

Where a compound (A) or a compound (B) can be present as mixtures of various possible isomeric forms, in particular of stereoisomers, such as, for example, E and Z, threo and erythro, and also optical isomers, and, if appropriate, also of tautomers. What is claimed are both the E and the Z isomers and the threo and erythro and also the optical isomers (R and S), any mixtures of these isomers, and also the possible tautomeric forms.

Compounds (A) or compounds (B) having at least one basic centre are capable of forming, for example, acid addition salts, e.g. with strong inorganic acids, such as mineral acids, e.g. perchloric acid, sulfuric acid, nitric acid, nitrous acid, a phosphoric acid or a hydrohalic acid, with strong organic carboxylic acids, such as unsubstituted substituted, e.g. halo-substituted, $C_1$-$C_4$ alkanecarboxylic acids, e.g. acetic acid, saturated or unsaturated dicarboxylic acids, e.g. oxalic, malonic, succinic, maleic, fumaric and phthalic acid, hydroxycarboxylic acids, e.g. ascorbic, lactic, malic, tartaric and citric acid, or benzoic acid, or with organic sulfonic acids, such as unsubstituted or substituted, e.g. halo-substituted, $C_1$-$C_4$alkane- or aryl-sulfonic acids, e.g. methane- or p-toluene-sulfonic acid. Compounds (A) or compounds (B) having at least one acid group are capable of forming, for example, salts with bases, e.g. metal salts, such as alkali metal or alkaline earth metal salts, e.g. sodium, potassium or magnesium salts, or salts with ammonia or an organic amine, such as morpholine, piperidine, pyrrolidine, a mono-, di- or tri-lower alkylamine, e.g. ethyl-, diethyl-, triethyl- or dimethyl-propyl-amine, or a mono-, di- or tri-hydroxy-lower alkylamine, e.g. mono-, di- or triethanolamine. In addition, corresponding internal salts may optionally be formed. In the context of the invention, preference is given to agrochemically advantageous salts. In view of the close relationship between the compounds (A) or the compounds (B) in free form and in the form of their salts, hereinabove and herein below any reference to the free compounds (A) or free compounds (B) or to their salts should be understood as including also the corresponding salts or the free compounds (A) or free compounds (B), respectively, where appropriate and expedient. The equivalent also applies to tautomers of compounds (A) or compounds (B) and to their salts.

According to the invention the expression "combination" stands for the various combinations of compounds (A) and (B), for example in a single "ready-mix" form, in a combined spray mixture composed from separate formulations of the single active compounds, such as a "tank-mix", and in a combined use of the single active ingredients when applied in a sequential manner, i.e. one after the other with a reasonably short period, such as a few hours or days. Preferably the order of applying the compounds (A) and (B) is not essential for working the present invention.

Plants

All plants and plant parts can be treated in accordance with the invention. Plants are understood here to mean all plants and plant populations, such as desired and undesired wild plants or crop plants (including naturally occurring crop plants). Crop plants may be plants which can be obtained by conventional breeding and optimization methods or by biotechnological and genetic engineering methods or combinations of these methods, including the transgenic plants and including the plant cultivars which are protectable and non-protectable by plant breeders' rights. Plant parts are understood to mean all parts and organs of plants above and below the ground, such as shoot, leaf, flower and root, examples of which include leaves, needles, stalks, stems, flowers, fruit bodies, fruits and seeds, and also roots, tubers and rhizomes. The plant parts also include harvested material and vegetative and generative propagation material, for example cuttings, tubers, rhizomes, slips and seeds.

Plants which can be treated in accordance with the invention include the following: cotton, flax, grapevine, fruit, vegetables, such as Rosaceae sp. (for example pome fruits such as apples and pears, but also stone fruits such as apricots, cherries, almonds and peaches, and soft fruits such as strawberries), Ribesioideae sp., Juglandaceae sp., Betulaceae sp., Anacardiaceae sp., Fagaceae sp., Moraceae sp., Oleaceae sp., Actinidaceae sp., Lauraceae sp., Musaceae sp. (for example banana trees and plantations), Rubiaceae sp. (for example coffee), Theaceae sp., Sterculiceae sp., Rutaceae sp. (for example lemons, oranges and grapefruit); Solanaceae sp. (for example tomatoes), Liliaceae sp., Asteraceae sp. (for example lettuce), Umbelliferae sp., Cruciferae sp., Chenopodiaceae sp., Cucurbitaceae sp. (for example cucumber), Alliaceae sp. (for example leek, onion), Papilionaceae sp. (for example peas); major crop plants, such as Gramineae sp. (for example maize, turf, cereals such as wheat, rye, rice, barley, oats, millet and triticale), Asteraceae sp. (for example sunflower), Brassicaceae sp. (for example white cabbage, red cabbage, broccoli, cauliflower, Brussels sprouts, pak Choi, kohlrabi, radishes, and oilseed rape, mustard, horseradish and cress), Fabacae sp. (for example bean, peanuts), Papilionaceae sp. (for example soya bean), Solanaceae sp. (for example potatoes), Chenopodiaceae sp. (for example sugar beet, fodder beet, swiss chard, beetroot); useful plants and ornamental plants for gardens and wooded areas; and genetically modified varieties of each of these plants.

Pathogens

Non-limiting examples of pathogens of fungal diseases which can be treated in accordance with the invention include:

diseases caused by powdery mildew pathogens, for example *Blumeria* species, for example *Blumeria graminis*; *Podosphaera* species, for example *Podosphaera leucotricha*; *Sphaerotheca* species, for example *Sphaerotheca fuliginea*; *Uncinula* species, for example *Uncinula necator*;

diseases caused by rust disease pathogens, for example *Gymnosporangium* species, for example *Gymnosporangium sabinae*; *Hemileia* species, for example *Hemileia vastatrix*; *Phakopsora* species, for example *Phakopsora pachyrhizi* or *Phakopsora meibomiae*; *Puccinia* species, for example *Puccinia recondita*, *Puccinia graminis* oder *Puccinia striiformis*; *Uromyces* species, for example *Uromyces appendiculatus*;

diseases caused by pathogens from the group of the Oomycetes, for example *Albugo* species, for example *Albugo candida*; *Bremia* species, for example *Bremia lactucae*; *Peronospora* species, for example *Peronospora pisi* or *P. brassicae*; *Phytophthora* species, for example *Phytophthora infestans*; *Plasmopara* species, for example *Plasmopara viticola*; *Pseudoperonospora* species, for example *Pseudoperonospora humuli* or *Pseudoperonospora cubensis*; *Pythium* species, for example *Pythium ultimum*;

leaf blotch diseases and leaf wilt diseases caused, for example, by *Alternaria* species, for example *Alternaria solani*; *Cercospora* species, for example *Cercospora beticola*; *Cladiosporium* species, for example *Cladiosporium cucumerinum*; *Cochliobolus* species, for example *Cochliobolus sativus* (conidial form: *Drechslera*, syn: *Helminthosporium*) or *Cochliobolus miyabeanus*; *Colletotrichum* species, for example *Colletotrichum lindemuthianium*; *Cycloconium* species, for example *Cycloconium oleaginum*; *Diaporthe* species, for example *Diaporthe citri*; *Elsinoe* species, for example *Elsinoe fawcettii* ; *Gloeosporium* species, for example *Gloeosporium laeticolor*; *Glomerella* species, for example *Glomerella cingulata*; *Guignardia* species, for example *Guignardia bidwelli*; *Leptosphaeria* species, for example *Leptosphaeria maculans*; *Magnaporthe* species, for example *Magnaporthe grisea*; *Microdochium* species, for example *Microdochium nivale*; *Mycosphaerella* species, for example *Mycosphaerella graminicola*, *Mycosphaerella arachidicola* or *Mycosphaerella fijiensis*; *Phaeosphaeria* species, for example *Phaeosphaeria nodorum*; *Pyrenophora* species, for example *Pyrenophora teres* or *Pyrenophora tritici repentis*; *Ramularia* species, for example *Ramularia collo-cygni* or *Ramularia areola*; *Rhynchosporium* species, for example *Rhynchosporium secalis*; *Septoria* species, for example *Septoria apii* or *Septoria lycopersici*; *Stagonospora* species, for example *Stagonospora nodorum*; *Typhula* species, for example *Typhula incarnata*; *Venturia* species, for example *Venturia inaequalis*;

root and stem diseases caused, for example, by *Corticium* species, for example *Corticium graminearum*; *Fusarium* species, for example *Fusarium oxysporum*; *Gaeumannomyces* species, for example *Gaeumannomyces graminis*; *Plasmodiophora* species, for example *Plasmodiophora brassicae*; *Rhizoctonia* species, for example *Rhizoctonia solani*; *Sarocladium* species, for example *Sarocladium oryzae*; *Sclerotium* species, for example *Sclerotium oryzae*; *Tapesia* species, for example *Tapesia acuformis*; *Thielaviopsis* species, for example *Thielaviopsis basicola*;

ear and panicle diseases (including corn cobs) caused, for example, by *Alternaria* species, for example *Alternaria* spp.; *Aspergillus* species, for example *Aspergillus flavus*; *Cladosporium* species, for example *Cladosporium cladosporioides*; *Claviceps* species, for example *Claviceps purpurea*; *Fusarium* species, for example *Fusarium culmorum*; *Gibberella* species, for example *Gibberella zeae*; *Monographella* species, for example *Monographella nivalis*; *Stagnospora* species, for example *Stagnospora nodorum*;

diseases caused by smut fungi, for example *Sphacelotheca* species, for example *Sphacelotheca reiliana*; *Tilletia* species, for example *Tilletia caries* or *Tilletia controversa*; *Urocystis* species, for example *Urocystis occulta*; *Ustilago* species, for example *Ustilago nuda*;

fruit rot caused, for example, by *Aspergillus* species, for example *Aspergillus flavus*; *Botrytis* species, for example *Botrytis cinerea*; *Penicillium* species, for example *Penicillium expansum* or *Penicillium purpurogenum*; *Rhizopus* species, for example *Rhizopus stolonifer*; *Sclerotinia* species, for example *Sclerotinia sclerotiorum*; *Verticilium* species, for example *Verticilium alboatrum*;

seed- and soil-borne rot and wilt diseases, and also diseases of seedlings, caused, for example, by *Alternaria* species, for example *Alternaria brassicicola*; *Aphanomyces* species, for example *Aphanomyces euteiches*; *Ascochyta* species, for example *Ascochyta lentis*; *Aspergillus* species, for example *Aspergillus flavus*; *Cladosporium* species, for example *Cladosporium herbarum*; *Cochliobolus* species, for example *Cochliobolus sativus* (conidial form: *Drechslera, Bipolaris* Syn: *Helminthosporium*); *Colletotrichum* species, for example *Colletotrichum coccodes*; *Fusarium* species, for example *Fusarium culmorum*; *Gibberella* species, for example *Gibberella zeae*; *Macrophomina* species, for example *Macrophomina phaseolina*; *Microdochium* species, for example *Microdochium nivale*; *Monographella* species, for example *Monographella nivalis*; *Penicillium* species, for example *Penicillium expansum*; *Phoma* species, for example *Phoma lingam*; *Phomopsis* species, for example *Phomopsis sojae*; *Phytophthora* species, for example *Phytophthora cactorum*; *Pyrenophora* species, for example *Pyrenophora graminea*; *Pyricularia* species, for example *Pyricularia oryzae*; *Pythium* species, for example *Pythium ultimum*; *Rhizoctonia* species, for example *Rhizoctonia solani*; *Rhizopus* species, for example *Rhizopus oryzae*; *Sclerotium* species, for example *Sclerotium rolfsii*; *Septoria* species, for example *Septoria nodorum*; *Typhula* species, for example *Typhula incarnata*; *Verticillium* species, for example *Verticillium dahliae*; cancers, galls and witches' broom caused, for example, by *Nectria* species, for example *Nectria galligena*; wilt diseases caused, for example, by *Monilinia* species, for example *Monilinia laxa*; deformations of leaves, flowers and fruits caused, for example, by Exobasidium species, for example *Exobasidium vexans*; *Taphrina* species, for example *Taphrina deformans*;

degenerative diseases in woody plants, caused, for example, by *Esca* species, for example *Phaeomoniella chlamydospora, Phaeoacremonium aleophilum* or *Fomitiporia mediterranea*; *Ganoderma* species, for example *Ganoderma boninense*;

diseases of flowers and seeds caused, for example, by *Botrytis* species, for example *Botrytis cinerea*;

diseases of plant tubers caused, for example, by *Rhizoctonia* species, for example *Rhizoctonia solani*; *Helminthosporium* species, for example *Helminthosporium solani*;

diseases caused by bacterial pathogens, for example *Xanthomonas* species, for example *Xanthomonas campestris* pv. *oryzae*; *Pseudomonas* species, for example *Pseudomonas syringae* pv. *lachrymans*; *Erwinia* species, for example *Erwinia amylovora*.

Preference is given to controlling the following diseases of soya beans:

Fungal diseases on leaves, stems, pods and seeds caused, for example, by *Alternaria* leaf spot (*Alternaria* spec. *atrans tenuissima*), Anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (Dactuliophora glycines), downy mildew (*Peronospora manshurica*), drechslera blight (*Drechslera glycine*), frogeye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi, Phakopsora meibomiae*), scab (*Sphaceloma glycines*), stemphylium leaf blight (*Stemphylium botryosum*), target spot (*Corynespora cassiicola*).

Fungal diseases on roots and the stem base caused, for example, by black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (Mycoleptodiscus *terrestris*), neocosmospora (Neocosmospora vasinfecta), pod and stem blight (*Diaporthe phaseolorum*), stem canker (*Diaporthe phaseolorum* var. caulivora), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

Plant Growth Regulation

In some cases, the inventive compositions can, at particular concentrations or application rates, also be used as herbicides, safeners, growth regulators or agents to improve plant properties, or as microbicides, for example as fungicides, antimycotics, bactericides, viricides (including compositions against viroids) or as compositions against MLO (*Mycoplasma*-like organisms) and RLO (*Rickettsia*-like organisms). If appropriate, they can also be used as intermediates or precursors for the synthesis of other active ingredients.

The inventive active combinations intervene in the metabolism of the plants and can therefore also be used as growth regulators.

Plant growth regulators may exert various effects on plants. The effect of the substances depends essentially on the time of application in relation to the developmental stage of the plant, and also on the amounts of active ingredient applied to the plants or their environment and on the type of application. In each case, growth regulators should have a particular desired effect on the crop plants.

Plant growth-regulating compounds can be used, for example, to inhibit the vegetative growth of the plants. Such inhibition of growth is of economic interest, for example, in the case of grasses, since it is thus possible to reduce the frequency of grass cutting in ornamental gardens, parks and sport facilities, on roadsides, at airports or in fruit crops. Also of significance is the inhibition of the growth of herbaceous and woody plants on roadsides and in the vicinity of pipelines or overhead cables, or quite generally in areas where vigorous plant growth is unwanted.

Also important is the use of growth regulators for inhibition of the longitudinal growth of cereal. This reduces or completely eliminates the risk of lodging of the plants prior to harvest. In addition, growth regulators in the case of cereals can strengthen the culm, which also counteracts lodging. The employment of growth regulators for shortening and strengthening culms allows the deployment of higher fertilizer volumes to increase the yield, without any risk of lodging of the cereal crop.

In many crop plants, inhibition of vegetative growth allows denser planting, and it is thus possible to achieve higher yields based on the soil surface. Another advantage of the smaller plants obtained in this way is that the crop is easier to cultivate and harvest.

Inhibition of the vegetative plant growth may also lead to enhanced yields because the nutrients and assimilates are of more benefit to flower and fruit formation than to the vegetative parts of the plants.

Frequently, growth regulators can also be used to promote vegetative growth. This is of great benefit when harvesting the vegetative plant parts. However, promoting vegetative growth may also promote generative growth in that more assimilates are formed, resulting in more or larger fruits.

In some cases, yield increases may be achieved by manipulating the metabolism of the plant, without any detectable changes in vegetative growth. In addition, growth regulators can be used to alter the composition of the plants, which in turn may result in an improvement in quality of the harvested products. For example, it is possible to increase the sugar content in sugar beet, sugar cane, pineapples and in citrus fruit, or to increase the protein content in soya or cereals. It is also possible, for example, to use growth regulators to inhibit the degradation of desirable ingredients, for example sugar in sugar beet or sugar cane, before or after harvest. It is also possible to positively influence the production or the elimination of secondary plant ingredients. One example is the stimulation of the flow of latex in rubber trees.

Under the influence of growth regulators, parthenocarpic fruits may be formed. In addition, it is possible to influence the sex of the flowers. It is also possible to produce sterile pollen, which is of great importance in the breeding and production of hybrid seed.

Use of growth regulators can control the branching of the plants. On the one hand, by breaking apical dominance, it is possible to promote the development of side shoots, which may be highly desirable particularly in the cultivation of ornamental plants, also in combination with an inhibition of growth. On the other hand, however, it is also possible to inhibit the growth of the side shoots. This effect is of particular interest, for example, in the cultivation of tobacco or in the cultivation of tomatoes.

Under the influence of growth regulators, the amount of leaves on the plants can be controlled such that defoliation of the plants is achieved at a desired time. Such defoliation plays a major role in the mechanical harvesting of cotton, but is also of interest for facilitating harvesting in other crops, for example in viticulture. Defoliation of the plants can also be undertaken to lower the transpiration of the plants before they are transplanted.

Growth regulators can likewise be used to regulate fruit dehiscence. On the one hand, it is possible to prevent premature fruit dehiscence. On the other hand, it is also possible to promote fruit dehiscence or even flower abortion to achieve a desired mass ("thinning"), in order to eliminate alternation. Alternation is understood to mean the characteristic of some fruit species, for endogenous reasons, to deliver very different yields from year to year. Finally, it is possible to use growth regulators at the time of harvest to reduce the forces required to detach the fruits, in order to allow mechanical harvesting or to facilitate manual harvesting.

Growth regulators can also be used to achieve faster or else delayed ripening of the harvested material before or after harvest. This is particularly advantageous as it allows optimal adjustment to the requirements of the market. Moreover, growth regulators in some cases can improve the fruit colour. In addition, growth regulators can also be used to concentrate maturation within a certain period of time. This establishes the prerequisites for complete mechanical or manual harvesting in a single operation, for example in the case of tobacco, tomatoes or coffee.

By using growth regulators, it is additionally possible to influence the resting of seed or buds of the plants, such that plants such as pineapple or ornamental plants in nurseries, for example, germinate, sprout or flower at a time when they are normally not inclined to do so. In areas where there is a risk of frost, it may be desirable to delay budding or germination of seeds with the aid of growth regulators, in order to avoid damage resulting from late frosts.

Finally, growth regulators can induce resistance of the plants to frost, drought or high salinity of the soil. This allows the cultivation of plants in regions which are normally unsuitable for this purpose.

Resistance Induction/Plant Health and Other Effects

The active combinations according to the invention also exhibit a potent strengthening effect in plants. Accordingly, they can be used for mobilizing the defences of the plant against attack by undesirable microorganisms.

Plant-strengthening (resistance-inducing) substances are to be understood as meaning, in the present context, those substances which are capable of stimulating the defence system of plants in such a way that the treated plants, when subsequently inoculated with undesirable microorganisms, develop a high degree of resistance to these microorganisms.

The active combinations according to the invention are also suitable for increasing the yield of crops. In addition, they show reduced toxicity and are well tolerated by plants.

Further, in context with the present invention plant physiology effects comprise the following:

Abiotic stress tolerance, comprising temperature tolerance, drought tolerance and recovery after drought stress, water use efficiency (correlating to reduced water consumption), flood tolerance, ozone stress and UV tolerance, tolerance towards chemicals like heavy metals, salts, pesticides (safener) etc.

Biotic stress tolerance, comprising increased fungal resistance and increased resistance against nematodes, viruses and bacteria. In context with the present invention, biotic stress tolerance preferably comprises increased fungal resistance and increased resistance against nematodes Increased plant vigor, comprising plant health/plant quality and seed vigor, reduced stand failure, improved appearance, increased recovery, improved greening effect and improved photosynthetic efficiency.

Effects on plant hormones and/or functional enzymes.

Effects on growth regulators (promoters), comprising earlier germination, better emergence, more developed root system and/or improved root growth, increased ability of filtering, more productive tillers, earlier flowering, increased plant height and/or biomass, shorting of stems, improvements in shoot growth, number of kernels/ear, number of ears/m$^2$, number of stolons and/or number of flowers, enhanced harvest index, bigger leaves, less dead basal leaves, improved phyllotaxy, earlier maturation/earlier fruit finish, homogenous riping, increased duration of grain filling, better fruit finish, bigger fruit/vegetable size, sprouting resistance and reduced lodging.

Increased yield, referring to total biomass per hectare, yield per hectare, kernel/fruit weight, seed size and/or hectoleter weight as well as to increased product quality, comprising:

improved processability relating to size distribution (kernel, fruit, etc.), homogenous riping, grain moisture, better milling, better vinification, better brewing, increased juice yield, harvestability, digestibility, sedimentation value, falling number, pod stability, storage stability, improved fiber length/strength/uniformity, increase of milk and/or meet quality of silage fed animals, adaption to cooking and flying;

further comprising improved marketability relating to improved fruit/grain quality, size distribution (kernel, fruit, etc.), increased storage/shelf-life, firmness/softness, taste (aroma, texture, etc.), grade (size, shape, number of berries, etc.), number of berries/fruits per bunch, crispness, freshness, coverage with wax, frequency of physiological disorders, colour, etc.;

further comprising increased desired ingredients such as e.g. protein content, fatty acids, oil content, oil quality, aminoacid composition, sugar content, acid content (pH), sugar/acid ratio (Brix), polyphenols, starch content, nutritional quality, gluten content/index, energy content, taste, etc.;

and further comprising decreased undesired ingredients such as e.g. less mycotoxins, less aflatoxins, geosmin level, phenolic aromas, lacchase, polyphenol oxidases and peroxidases, nitrate content etc.

Sustainable agriculture, comprising nutrient use efficiency, especially nitrogen (N)-use efficiency, phosphours (P)-use efficiency, water use efficiency, improved transpiration, respiration and/or $CO_2$ assimilation rate, better nodulation, improved Ca-metabolism etc.

Delayed senescence, comprising improvement of plant physiology which is manifested, for example, in a longer grain filling phase, leading to higher yield, a longer duration of green leaf colouration of the plant and thus comprising colour (greening), water content, dryness etc. Accordingly, in the context of the present invention, it has been found that the specific inventive application of the active compound combination makes it possible to prolong the green leaf area duration, which delays the maturation (senescence) of the plant. The main advantage to the farmer is a longer grain filling phase leading to higher yield. There is also an advantage to the farmer on the basis of greater flexibility in the harvesting time.

Therein "sedimentation value" is a measure for protein quality and describes according to Zeleny (Zeleny value) the degree of sedimentation of flour suspended in a lactic acid solution during a standard time interval. This is taken as a measure of the baking quality. Swelling of the gluten fraction of flour in lactic acid solution affects the rate of sedimentation of a flour suspension. Both a higher gluten content and a better gluten quality give rise to slower sedimentation and higher Zeleny test values. The sedimentation value of flour depends on the wheat protein composition and is mostly correlated to the protein content, the wheat hardness, and the volume of pan and hearth loaves. A stronger correlation between loaf volume and Zeleny sedimentation volume compared to SDS sedimentation volume could be due to the protein content influencing both the volume and Zeleny value (*Czech J. Food Sci. Vol.* 21, No. 3: 91-96, 2000).

Further the "falling number" as mentioned herein is a measure for the baking quality of cereals, especially of wheat. The falling number test indicates that sprout damage may have occurred. It means that changes to the physical properties of the starch portion of the wheat kernel has already happened. Therein, the falling number instrument analyzes viscosity by measuring the resistance of a flour and water paste to a falling plunger. The time (in seconds) for this to happen is known as the falling number. The falling number results are recorded as an index of enzyme activity in a wheat or flour sample and results are expressed in time as seconds. A high falling number (for example, above 300 seconds) indicates minimal enzyme activity and sound quality wheat or flour. A low falling number (for example, below 250 seconds) indicates substantial enzyme activity and sprout-damaged wheat or flour.

The term "more developed root system"/"improved root growth" refers to longer root system, deeper root growth, faster root growth, higher root dry/fresh weight, higher root volume, larger root surface area, bigger root diameter, higher root stability, more root branching, higher number of root hairs, and/or more root tips and can be measured by analyzing the root architecture with suitable methodologies and Image analysis programmes (e.g. WinRhizo).

The term "crop water use efficiency" refers technically to the mass of agriculture produce per unit water consumed and economically to the value of product(s) produced per unit water volume consumed and can e.g. be measured in terms of yield per ha, biomass of the plants, thousand-kernel mass, and the number of ears per m2.

The term "nitrogen-use efficiency" refers technically to the mass of agriculture produce per unit nitrogen consumed and economically to the value of product(s) produced per unit nitrogen consumed, reflecting uptake and utilization efficiency.

Improvement in greening/improved colour and improved photosynthetic efficiency as well as the delay of senescence can be measured with well-known techniques such as a HandyPea system (Hansatech). Fv/Fm is a parameter widely used to indicate the maximum quantum efficiency of photosystem II (PSII). This parameter is widely considered to be a selective indication of plant photosynthetic performance with healthy samples typically achieving a maximum Fv/Fm value of approx. 0.85. Values lower than this will be observed if a sample has been exposed to some type of biotic or abiotic stress factor which has reduced the capacity for photochemical quenching of energy within PSII. Fv/Fm is presented as a ratio of variable fluorescence (Fv) over the maximum fluorescence value (Fm). The Performance Index is essentially an indicator of sample vitality. (See e.g. *Advanced Techniques in Soil Microbiology,* 2007, 11, 319-341; *Applied Soil Ecology,* 2000, 15, 169-182.)

The improvement in greening/improved colour and improved photosynthetic efficiency as well as the delay of senescence can also be assessed by measurement of the net photosynthetic rate (Pn), measurement of the chlorophyll content, e.g. by the pigment extraction method of Ziegler and Ehle, measurement of the photochemical efficiency (Fv/Fm ratio), determination of shoot growth and final root and/or canopy biomass, determination of tiller density as well as of root mortality.

Within the context of the present invention preference is given to improving plant physiology effects which are selected from the group comprising: enhanced root growth/more developed root system, improved greening, improved water use efficiency (correlating to reduced water consumption), improved nutrient use efficiency, comprising especially improved nitrogen (N)-use efficiency, delayed senescence and enhanced yield.

Within the enhancement of yield preference is given as to an improvement in the sedimentation value and the falling number as well as to the improvement of the protein and sugar content—especially with plants selected from the group of cereals (preferably wheat).

Preferably the novel use of the fungicidal compositions of the present invention relates to a combined use of a) preventively and/or curatively controlling pathogenic fungi and/or nematodes, with or without resistance management, and b) at least one of enhanced root growth, improved greening, improved water use efficiency, delayed senescence and enhanced yield. From group b) enhancement of root system, water use efficiency and N-use efficiency is particularly preferred.

Mycotoxins

In addition, the active compound combination of the present invention can reduce the mycotoxin content in the harvested material and the foods and feeds prepared therefrom. Mycotoxins include particularly, but not exclusively, the following: deoxynivalenol (DON), nivalenol, 15-Ac- DON, 3-Ac-DON, T2- and HT2-toxin, fumonisins, zearalenon, moniliformin, fusarin, diaceotoxyscirpenol (DAS), beauvericin, enniatin, fusaroproliferin, fusarenol, ochratoxins, patulin, ergot alkaloids and aflatoxins which can be produced, for example, by the following fungi: *Fusarium* spec., such as *F. acuminatum, F. asiaticum, F. avenaceum, F. crookwellense, F. culmorum, F. graminearum* (*Gibberella zeae*), *F. equiseti, F. fujikoroi, F. musarum, F. oxysporum, F. proliferatum, F. poae, F. pseudograminearum, F. sambucinum, F. scirpi, F. semitectum, F. solani, F. sporotrichoides, F. langsethiae, F. subglutinans, F. tricinctum, F. verticillioides* etc., and also by *Aspergillus* spec., such as *A. flavus, A. parasiticus, A. nomius, A. ochraceus, A. clavatus, A. terreus, A. versicolor, Penicillium* spec., such as *P. verrucosum, P. viridicatum, P. citrinum, P. expansum, P. claviforme, P. roqueforti, Claviceps* spec., such as *C. purpurea, C. fusiformis, C. paspali, C. africana, Stachy botrys* spec. and others.

Material Protection

The the active compound combination of the present invention can also be used in the protection of materials, for protection of industrial materials against attack and destruction by phytopathogenic fungi.

In addition, the the active compound combination of the present invention can be used as antifouling compositions, alone or in combinations with other active ingredients.

Industrial materials in the present context are understood to mean inanimate materials which have been prepared for use in industry. For example, industrial materials which are to be protected by inventive compositions from microbial alteration or destruction may be adhesives, glues, paper, wallpaper and board/cardboard, textiles, carpets, leather, wood, fibers and tissues, paints and plastic articles, cooling lubricants and other materials which can be infected with or destroyed by microorganisms. Parts of production plants and buildings, for example cooling-water circuits, cooling and heating systems and ventilation and air-conditioning units, which may be impaired by the proliferation of microorganisms may also be mentioned within the scope of the materials to be protected. Industrial materials within the scope of the present invention preferably include adhesives, sizes, paper and card, leather, wood, paints, cooling lubricants and heat transfer fluids, more preferably wood.

The the active compound combination of the present invention may prevent adverse effects, such as rotting, decay, discoloration, decoloration or formation of mould.

In the case of treatment of wood the the active compound combination of the present invention may also be used against fungal diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting a composition according to the invention; this includes for example direct application, spraying, dipping, injection or any other suitable means.

In addition, the the active compound combination of the present invention can be used to protect objects which come into contact with saltwater or brackish water, especially hulls, screens, nets, buildings, moorings and signalling systems, from fouling.

The the active compound combination of the present invention can also be employed for protecting storage goods. Storage goods are understood to mean natural substances of vegetable or animal origin or processed products thereof which are of natural origin, and for which long-term protection is desired. Storage goods of vegetable origin, for example plants or plant parts, such as stems, leaves, tubers, seeds, fruits, grains, can be protected freshly harvested or after processing by (pre)drying, moistening, comminuting, grinding, pressing or roasting. Storage goods also include timber, both unprocessed, such as construction timber, electricity poles and barriers, or in the form of finished products, such as furniture. Storage goods of animal origin are, for example, hides, leather, furs and hairs. The inventive compositions may prevent adverse effects, such as rotting, decay, discoloration, decoloration or formation of mould.

Microorganisms capable of degrading or altering the industrial materials include, for example, bacteria, fungi, yeasts, algae and slime organisms. The the active compound combination of the present invention preferably act against fungi, especially moulds, wood-discoloring and wood-destroying fungi (Ascomycetes, Basidiomycetes, Deuteromycetes and Zygomycetes), and against slime organisms and algae. Examples include microorganisms of the following genera: *Alternaria*, such as *Alternaria tenuis*; *Aspergillus*, such as *Aspergillus niger*; *Chaetomium*, such as *Chaetomium globosum*; *Coniophora*, such as *Coniophora puetana*; *Lentinus*, such as *Lentinus tigrinus*; *Penicillium*, such as *Penicillium glaucum*; *Polyporus*, such as *Polyporus versicolor*; *Aureobasidium*, such as *Aureobasidium pullulans*; *Sclerophoma*, such as *Sclerophoma pityophila*; *Trichoderma*, such as *Trichoderma viride*; *Ophiostoma* spp., *Ceratocystis* spp., *Humicola* spp., *Petriella* spp., *Trichurus* spp., *Coriolus* spp., *Gloeophyllum* spp., *Pleurotus* spp., *Poria* spp., *Serpula* spp. and *Tyromyces* spp., *Cladosporium* spp., *Paecilomyces* spp. *Mucor* spp., *Escherichia*, such as *Escherichia coli*; *Pseudomonas*, such as *Pseudomonas aeruginosa*; *Staphylococcus*, such as *Staphylococcus aureus, Candida* spp. and *Saccharomyces* spp., such as *Saccharomyces cerevisae*.

Formulations

The present invention furthermore relates to compositions for combating/controlling undesirable microorganisms comprising the active compound combinations according to the invention. Preferably, the compositions are fungicidal compositions comprising agriculturally suitable auxiliaries, solvents, carriers, surfactants or extenders.

According to the invention, a carrier is a natural or synthetic, organic or inorganic substance with which the active ingredients are mixed or combined for better applicability, in particular for application to plants or plant parts or seed. The carrier, which may be solid or liquid, is generally inert and should be suitable for use in agriculture.

Useful solid carriers include: for example ammonium salts and natural rock flours, such as kaolins, clays, talc, chalk, quartz, attapulgite, montmorillonite or diatomaceous earth, and synthetic rock flours, such as finely divided silica, alumina and silicates; useful solid carriers for granules include: for example, crushed and fractionated natural rocks such as calcite, marble, pumice, sepiolite and dolomite, and also synthetic granules of inorganic and organic flours, and granules of organic material such as paper, sawdust, coconut shells, maize cobs and tobacco stalks; useful emulsifiers and/or foam-formers include: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the alcohol-POE and/or -POP ethers, acid and/or POP POE esters, alkylaryl and/or POP POE ethers, fat and/or POP POE adducts, POE- and/or POP-polyol derivatives, POE- and/or POP-sorbitan or -sugar adducts, alkyl or aryl sulphates, alkyl- or arylsulphonates and alkyl or aryl phosphates or the corresponding PO-ether adducts. Additionally suitable are oligo- or polymers, for example those derived from vinylic monomers, from acrylic acid, from EO and/or PO alone or in combination with, for example, (poly)alcohols or (poly)amines. It is also possible to use lignin and its sulphonic acid derivatives, unmodified and modified celluloses, aromatic and/or aliphatic sulphonic acids and also their adducts with formaldehyde.

The active ingredients can be converted to the customary formulations, such as solutions, emulsions, wettable powders, water- and oil-based suspensions, powders, dusts, pastes, soluble powders, soluble granules, granules for broadcasting, suspoemulsion concentrates, natural products impregnated with active ingredient, synthetic substances impregnated with active ingredient, fertilizers and also microencapsulations in polymeric substances.

The active ingredients can be applied as such, in the form of their formulations or the use forms prepared therefrom, such as ready-to-use solutions, emulsions, water- or oil-based suspensions, powders, wettable powders, pastes, soluble powders, dusts, soluble granules, granules for broadcasting, suspoemulsion concentrates, natural products impregnated with active ingredient, synthetic substances impregnated with active ingredient, fertilizers and also microencapsulations in polymeric substances. Application is accomplished in a customary manner, for example by watering, spraying, atomizing, broadcasting, dusting, foaming, spreading-on and the like. It is also possible to deploy the active ingredients by the ultra-low volume method or to inject the active ingredient preparation/the active ingredient itself into the soil. It is also possible to treat the seed of the plants.

The formulations mentioned can be prepared in a manner known per se, for example by mixing the active ingredients with at least one customary extender, solvent or diluent, emulsifier, dispersant and/or binder or fixing agent, wetting agent, a water repellent, if appropriate siccatives and UV stabilizers and if appropriate dyes and pigments, antifoams, preservatives, secondary thickeners, stickers, gibberellins and also other processing auxiliaries.

The present invention includes not only formulations which are already ready for use and can be deployed with a suitable apparatus to the plant or the seed, but also commercial concentrates which have to be diluted with water prior to use.

The active compound combination of the present invention may be present as such or in their (commercial) formulations and in the use forms prepared from these formulations as a mixture with other (known) active ingredients, such as insecticides, attractants, sterilants, bactericides, acaricides, nematicides, fungicides, growth regulators, herbicides, fertilizers, safeners and/or semiochemicals.

The auxiliaries used may be those substances which are suitable for imparting particular properties to the composition itself or and/or to preparations derived therefrom (for example spray liquors, seed dressings), such as certain technical properties and/or also particular biological properties. Typical auxiliaries include: extenders, solvents and carriers.

Suitable extenders are, for example, water, polar and nonpolar organic chemical liquids, for example from the classes of the aromatic and nonaromatic hydrocarbons (such as paraffins, alkylbenzenes, alkylnaphthalenes, chlorobenzenes), the alcohols and polyols (which may optionally also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

Liquefied gaseous extenders or carriers are understood to mean liquids which are gaseous at standard temperature and under standard pressure, for example aerosol propellants such as halohydrocarbons, or else butane, propane, nitrogen and carbon dioxide.

In the formulations it is possible to use tackifiers such as carboxymethylcellulose, natural and synthetic polymers in the form of powders, granules or latices, such as gum arabic, polyvinyl alcohol and polyvinyl acetate, or else natural phospholipids such as cephalins and lecithins and synthetic phospholipids. Further additives may be mineral and vegetable oils.

If the extender used is water, it is also possible to use, for example, organic solvents as auxiliary solvents. Useful liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water.

active compound combination of the present invention may additionally comprise further components, for example surfactants. Suitable surfactants are emulsifiers and/or foam formers, dispersants or wetting agents having ionic or nonionic properties, or mixtures of these surfactants. Examples thereof are salts of polyacrylic acid, salts of lignosulphonic acid, salts of phenolsulphonic acid or naphthalenesulphonic acid, polycondensates of ethylene oxide with fatty alcohols or with fatty acids or with fatty amines, substituted phenols (preferably alkylphenols or arylphenols), salts of sulphosuccinic esters, taurine derivatives (preferably alkyl taurates), phosphoric esters of polyethoxylated alcohols or phenols, fatty esters of polyols, and derivatives of the compounds containing sulphates, sulphonates and phosphates, for example alkylaryl polyglycol ethers, alkylsulphonates, alkyl sulphates, arylsulphonates, protein hydrolysates, lignosulphite waste liquors and methylcellulose. The presence of a surfactant is necessary if one of the active ingredients and/or one of the inert carriers is insoluble in water and when application is effected in water. The proportion of surfactants is between 5 and 40 percent by weight of the inventive composition.

It is possible to use dyes such as inorganic pigments, for example iron oxide, titanium oxide and Prussian Blue, and organic dyes such as alizarin dyes, azo dyes and metal phthalocyanine dyes, and trace nutrients such as salts of iron, manganese, boron, copper, cobalt, molybdenum and zinc.

Further additives may be perfumes, mineral or vegetable, optionally modified oils, waxes and nutrients (including trace nutrients), such as salts of iron, manganese, boron, copper, cobalt, molybdenum and zinc.

Additional components may be stabilizers, such as cold stabilizers, preservatives, antioxidants, light stabilizers, or other agents which improve chemical and/or physical stability.

If appropriate, other additional components may also be present, for example protective colloids, binders, adhesives, thickeners, thixotropic substances, penetrants, stabilizers, sequestering agents, complex formers. In general, the active ingredients can be combined with any solid or liquid additive commonly used for formulation purposes.

The formulations contain generally between 0.05 and 99% by weight, 0.01 and 98% by weight, preferably between 0.1 and 95% by weight, more preferably between 0.5 and 90% of active ingredient, most preferably between 10 and 70 percent by weight.

The formulations described above can be used for controlling unwanted microorganisms, in which the active compound combination of the present invention are applied to the microorganisms and/or in their habitat.

Seed Treatment

The invention furthermore includes a method for treating seed.

A further aspect of the present invention relates in particular to seeds (dormant, primed, pregerminated or even with emerged roots and leaves) treated with at least one of the active compound combinations of the present invention. The inventive seeds are used in methods for protection of seeds and emerged plants from the seeds from phytopathogenic harmful fungi. In these methods, seed treated with at least one inventive active ingredient is used.

The active compound combination of the present invention is also suitable for the treatment of seeds and young seedlings. A large part of the damage to crop plants caused by harmful organisms is triggered by the infection of the seeds before sowing or after germination of the plant. This phase is particularly critical since the roots and shoots of the growing plant are particularly sensitive, and even small damage may result in the death of the plant. Accordingly, there is great interest in protecting the seed and the germinating plant by using appropriate compositions.

It is also desirable to optimize the amount of the active ingredient used so as to provide the best possible protection for the seeds, the germinating plants and emerged seedlings from attack by phytopathogenic fungi, but without damaging the plants themselves by the active ingredient used. In particular, methods for the treatment of seed should also take into consideration the intrinsic phenotypes of transgenic plants in order to achieve optimum protection of the seed and the germinating plant with a minimum of crop protection compositions being employed.

The present invention therefore also relates to a method for protecting seeds, germinating plants and emerged seedlings against attack by animal pests and/or phytopathogenic harmful microorganisms by treating the seeds with an inventive composition. The invention also relates to the use of the compositions according to the invention for treating seeds for protecting the seeds, the germinating plants and emerged seedlings against animal pests and/or phytopathogenic microorganisms. The invention further relates to seeds which has been treated with an inventive composition for protection from animal pests and/or phytopathogenic microorganisms.

One of the advantages of the present invention is that the treatment of the seeds with these compositions not only protects the seed itself, but also the resulting plants after emergence, from animal pests and/or phytopathogenic harmful microorganisms. In this way, the immediate treatment of the crop at the time of sowing or shortly thereafter protect plants as well as seed treatment in prior to sowing. It is likewise considered to be advantageous that the inventive active ingredients or compositions can be used especially also for transgenic seed, in which case the plant which grows from this seed is capable of expressing a protein which acts against pests, herbicidal damage or abiotic stress. The treatment of such seeds with the inventive active ingredients or compositions, for example an insecticidal protein, can result in control of certain pests. Surprisingly, a further synergistic effect can be observed in this case, which additionally increases the effectiveness for protection against attack by pests, microorganisms, weeds or abiotic stress.

The active compound combination of the present invention are suitable for protection of seed of any plant variety which is used in agriculture, in the greenhouse, in forests or in horticulture. More particularly, the seed is that of cereals (such as wheat, barley, rye, millet and oats), oilseed rape, maize, cotton, soybeen, rice, potatoes, sunflower, beans, coffee, beet (e.g. sugar beet and fodder beet), peanut, vegetables (such as tomato, cucumber, onions and lettuce), lawns and ornamental plants. Of particular significance is the treatment of the seed of wheat, soybean, oilseed rape, maize and rice.

As also described below, the treatment of transgenic seed with the inventive active ingredients or compositions is of particular significance. This refers to the seed of plants containing at least one heterologous gene which allows the expression of a polypeptide or protein, e.g. having insecticidal properties. These heterologous genes in transgenic seeds may originate, for example, from microorganisms of the species *Bacillus, Rhizobium, Pseudomonas, Serratia, Trichoderma, Clavibacter, Glomus* or *Gliocladium*. These heterologous genes preferably originates from *Bacillus* sp., in which case the gene product is effective against the European corn borer and/or the Western corn rootworm. Particularly preferably, the heterologous genes originate from *Bacillus thuringiensis*.

In the context of the present invention, the inventive composition is applied to seeds either alone or in a suitable formulation. Preferably, the seed is treated in a state in which it is sufficiently stable for no damage to occur in the course of treatment. In general, seeds can be treated at any time between harvest and some time after sowing. It is customary to use seed which has been separated from the plant and freed from cobs, shells, stalks, coats, hairs or the flesh of the fruits. For example, it is possible to use seed which has been harvested, cleaned and dried down to a moisture content of less than 15% by weight. Alternatively, it is also possible to use seed which, after drying, for example, has been treated with water and then dried again, or seeds just after priming, or seeds stored in primed conditions or pre-germinated seeds, or seeds sown on nursery trays, tapes or paper.

When treating the seeds, it generally has to be ensured that the amount of the inventive composition applied to the seed and/or the amount of further additives is selected such that the germination of the seed is not impaired, or that the resulting plant is not damaged. This must be ensured particularly in the case of active ingredients which can exhibit phytotoxic effects at certain application rates.

The active compound combination of the present invention can be applied directly, i.e. without containing any other components and without having been diluted. In general, it is preferable to apply the compositions to the seed in the form of a suitable formulation. Suitable formulations and methods for seed treatment are known to those skilled in the art. The active compound combination of the present invention can be converted to the customary formulations relevant to on-seed applications, such as solutions, emulsions, suspensions, powders, foams, slurries or combined with other coating compositions for seed, such as film forming materials, pelleting materials, fine iron or other metal powders, granules, coating material for inactivated seeds, and also ULV formulations.

These formulations are prepared in a known manner, by mixing the active ingredients or active ingredient combinations with customary additives, for example customary extenders and solvents or diluents, dyes, wetting agents, dispersants, emulsifiers, antifoams, preservatives, secondary thickeners, adhesives, gibberellins, and also water.

Useful dyes which may be present in the seed dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed dressing formulations usable in accordance with the invention are all substances which promote wetting and which are conventionally used for the formulation of active agrochemical ingredients. Usable with preference are alkylnaphthalenesulphonates, such as diisopropyl- or diisobutylnaphthalenesulphonates.

Useful dispersants and/or emulsifiers which may be present in the seed dressing formulations usable in accordance with the invention are all nonionic, anionic and cationic dispersants conventionally used for the formulation of active agrochemical ingredients. Usable with preference are nonionic or anionic dispersants or mixtures of nonionic or anionic dispersants. Useful nonionic dispersants include especially ethylene oxide/propylene oxide block polymers, alkylphenol polyglycol ethers and tristryrylphenol polyglycol ether, and the phosphated or sulphated derivatives thereof. Suitable anionic dispersants are especially lignosulphonates, polyacrylic acid salts and arylsulphonate/formaldehyde condensates.

Antifoams which may be present in the seed dressing formulations usable in accordance with the invention are all foam-inhibiting substances conventionally used for the formulation of active agrochemical ingredients. Silicone antifoams and magnesium stearate can be used with preference.

Preservatives which may be present in the seed dressing formulations usable in accordance with the invention are all substances usable for such purposes in agrochemical compositions. Examples include dichlorophen and benzyl alcohol hemiformal.

Secondary thickeners which may be present in the seed dressing formulations usable in accordance with the invention are all substances usable for such purposes in agrochemical compositions. Preferred examples include cellulose derivatives, acrylic acid derivatives, xanthan, modified clays and finely divided silica.

Adhesives which may be present in the seed dressing formulations usable in accordance with the invention are all customary binders usable in seed dressing products. Preferred examples include polyvinylpyrrolidone, polyvinyl acetate, polyvinyl alcohol and tylose.

The formulations for on-seed applications usable in accordance with the invention can be used to treat a wide variety of different kinds of seed either directly or after prior dilution with water. For instance, the concentrates or the preparations obtainable therefrom by dilution with water can be used to dress the seed of cereals, such as wheat, barley, rye, oats, and triticale, and also seeds of maize, soybean, rice, oilseed rape, peas, beans, cotton, sunflowers, and beets, or else a wide variety of different vegetable seeds. The formulations usable in accordance with the invention, or the dilute preparations thereof, can also be used for seeds of transgenic plants. In this case, additional synergistic effects may also occur in interaction with the substances formed by expression.

For treatment of seeds with the formulations usable in accordance with the invention, or the preparations prepared therefrom by adding water, all mixing units usable customarily for on-seed applications are useful. Specifically, the procedure in on-seed applications is to place the seeds into a mixer, to add the particular desired amount of the formulations, either as such or after prior dilution with water, and to mix everything until all applied formulations are distributed homogeneously on the seeds. If appropriate, this is followed by a drying operation.

The application rate of the formulations usable in accordance with the invention can be varied within a relatively wide range. It is guided by the particular content of the active ingredients in the formulations and by the seeds. The application rates of each single active ingredient is generally between 0.001 and 15 g per kilogram of seed, preferably between 0.01 and 5 g per kilogram of seed.

Antimycotic Effects

In addition, the active compound combination of the present invention also have very good antimycotic effects. They have a very broad antimycotic activity spectrum, especially against dermatophytes and yeasts, moulds and diphasic fungi (for example against *Candida* species, such as *Candida albicans, Candida glabrata*), and *Epidermophyton floccosum, Aspergillus* species, such as *Aspergillus niger* and *Aspergillus fumigatus, Trichophyton* species, such as *Trichophyton mentagrophytes*, Microsporon species such as Microsporon *canis* and *audouinii*. The enumeration of these fungi by no means constitutes a restriction of the mycotic spectrum covered, and is merely of illustrative character.

The compounds can be used also to control important fungal pathogens in fish and crustacea farming, e.g. *saprolegnia diclina* in trouts, *saprolegnia parasitica* in crayfish.

The active compound combination of the present invention can therefore be used both in medical and in non-medical applications.

The active compound combination of the present invention can be used as such, in the form of their formulations or the use forms prepared therefrom, such as ready-to-use solutions, suspensions, wettable powders, pastes, soluble powders, dusts and granules. Application is accomplished in a customary manner, for example by watering, spraying, atomizing, broadcasting, dusting, foaming, spreading-on and the like. It is also possible to deploy the active ingredients by the ultra-low volume method or to inject the active ingredient preparation/the active ingredient itself into the soil. It is also possible to treat the seed of the plants.

GMO

As already mentioned above, it is possible to treat all plants and their parts in accordance with the invention. In a preferred embodiment, wild plant species and plant cultivars, or those obtained by conventional biological breeding methods, such as crossing or protoplast fusion, and also parts thereof, are treated. In a further preferred embodiment, transgenic plants and plant cultivars obtained by genetic engineering methods, if appropriate in combination with conventional methods (Genetically Modified Organisms), and parts thereof are treated. The terms "parts" or "parts of plants" or "plant parts" have been explained above. More preferably, plants of the plant cultivars which are commercially available or are in use are treated in accordance with the invention. Plant cultivars are understood to mean plants which have new properties ("traits") and have been obtained by conventional breeding, by mutagenesis or by recombinant DNA techniques. They can be cultivars, varieties, bio- or genotypes.

The method of treatment according to the invention can be used in the treatment of genetically modified organisms (GMOs), e.g. plants or seeds. Genetically modified plants (or transgenic plants) are plants of which a heterologous gene has been stably integrated into genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example, antisense technology, cosuppression technology, RNA interference-RNAi-technology or microRNA-miRNA-technology). A heterologous gene that is located in the genome is also called a transgene. A transgene that is defined by its particular location in the plant genome is called a transformation or transgenic event.

Plants and plant cultivars which are preferably to be treated according to the invention include all plants which have genetic material which impart particularly advantageous, useful traits to these plants (whether obtained by breeding and/or biotechnological means).

Plants and plant cultivars which are also preferably to be treated according to the invention are resistant against one or more biotic stresses, i.e. said plants show a better defense against animal and microbial pests, such as against nematodes, insects, mites, phytopathogenic fungi, bacteria, viruses and/or viroids.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients, shade avoidance.

Plants and plant cultivars which may also be treated according to the invention, are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content and composition for example cotton or starch, protein content, oil content and composition, nutritional value, reduction in anti-nutritional compounds, improved processability and better storage stability.

Plants that may be treated according to the invention are hybrid plants that already express the characteristic of heterosis or hybrid vigor which results in generally higher yield, vigor, health and resistance towards biotic and abiotic stresses).

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance.

Plants or plant cultivars (obtained by plant biotechnology methods such as genetic engineering) which may also be treated according to the invention show altered quantity, quality and/or storage-stability of the harvested product and/or altered properties of specific ingredients of the harvested product.

Plants or plant cultivars (that can be obtained by plant biotechnology methods such as genetic engineering) which may also be treated according to the invention are plants, such as cotton plants, with altered fiber characteristics. Such plants can be obtained by genetic transformation, or by selection of plants contain a mutation imparting such altered fiber characteristics.

Plants or plant cultivars (that can be obtained by plant biotechnology methods such as genetic engineering) which may also be treated according to the invention are plants, such as oilseed rape or related *Brassica* plants, with altered oil profile characteristics. Such plants can be obtained by genetic transformation, or by selection of plants contain a mutation imparting such altered oil profile characteristics.

Plants or plant cultivars (that can be obtained by plant biotechnology methods such as genetic engineering) which may also be treated according to the invention are plants, such as oilseed rape or related *Brassica* plants, with altered seed shattering characteristics. Such plants can be obtained by genetic transformation, or by selection of plants contain a mutation imparting such altered seed shattering characteristics and include plants such as oilseed rape plants with delayed or reduced seed shattering.

Plants or plant cultivars (that can be obtained by plant biotechnology methods such as genetic engineering) which may also be treated according to the invention are plants, such as Tobacco plants, with altered posttranslational protein modification patterns.

Application Rates

When using the active compound combination of the present invention, the application rates can be varied within a relatively wide range, depending on the kind of application. The application rate of the inventive active ingredients is in the case of treatment of plant parts, for example leaves: from 0.1 to 10 000 g/ha, preferably from 10 to 1000 g/ha, more preferably from 50 to 300 g/ha (in the case of application by watering or dripping, it is even possible to reduce the application rate, especially when inert substrates such as rock-wool or perlite are used);

in the case of seed treatment: from 0.1 to 200 g per 100 kg of seed, preferably from 1 to 150 g per 100 kg of seed, more preferably from 2.5 to 25 g per 100 kg of seed, even more preferably from 2.5 to 12.5 g per 100 kg of seed;

in the case of soil treatment: from 0.1 to 10 000 g/ha, preferably from 1 to 5000 g/ha.

These application rates are merely by way of example and are not limiting for the purposes of the invention.

EXAMPLES

The advanced fungicidal activity of the active compound combinations according to the invention is evident from the example below. While the individual active compounds exhibit weaknesses with regard to the fungicidal activity, the combinations have an activity which exceeds a simple addition of activities.

A synergistic effect of fungicides is always present when the fungicidal activity of the active compound combinations exceeds the total of the activities of the active compounds when applied individually. The expected activity for a given combination of two active compounds can be calculated as follows (cf. Colby, S. R., "Calculating Synergistic and Antagonistic Responses of Herbicide Combinations", Weeds 1967, 15, 20-22):

If

X is the efficacy when active compound A is applied at an application rate of m ppm (or g/ha), Y is the efficacy when active compound B is applied at an application rate of n ppm (or g/ha), E is the efficacy when the active compounds A and B are applied at application rates of m and n ppm (or g/ha), respectively, and then $$E = X + Y - \frac{X \cdot Y}{100}$$

The degree of efficacy, expressed in % is denoted. 0% means an efficacy which corresponds to that of the control while an efficacy of 100% means that no disease is observed.

If the actual fungicidal activity exceeds the calculated value, then the activity of the combination is super-additive, i.e. a synergistic effect exists. In this case, the efficacy which was actually observed must be greater than the value for the expected efficacy (E) calculated from the abovementioned formula.

A further way of demonstrating a synergistic effect is the method of Tammes (cf. "Isoboles, a graphic representation of synergism in pesticides" in Neth. J. Plant Path., 1964, 70, 73-80).

The invention is illustrated by the following examples. However the invention is not limited to the examples.

Example: In Vivo Preventive Test on Alternaria Test (Tomatoes)

| Solvent: | 24.5 parts by weight of acetone |
| | 24.5 parts by weight of dimethylacetamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration. To test for preventive activity, young plants are sprayed with the preparation of active compound at the stated rate of application. After the spray coating has dried on, the plants are inoculated with an aqueous spore suspension of Alternaria solani. The plants are then placed in an incubation cabinet at approximately 20° C. and a relative atmospheric humidity of 100%.

The test is evaluated 3 days after the inoculation. 0% means an efficacy which corresponds to that of the untreated control while an efficacy of 100% means that no disease is observed. The table below clearly shows that the observed activity of the active compound combination according to the invention is greater than the calculated activity, i.e. a synergistic effect is present.

TABLE in vivo preventive test on Alternaria test (tomatoes)

| | Active compounds | Application rate of active compound in ppm a.i. | Efficacy in % found* | calc.** |
|---|---|---|---|---|
| (I-3) | 2-(difluoromethyl)-N-(3-ethyl-1,1-dimethyl-2,3-dihydro-1H-inden-4-yl)nicotinamide | 1 | 45 | |
| | | 0.5 | 45 | |
| | | 0.25 | 15 | |
| (I-4) | 2-(difluoromethyl)-N-[(3R)-3-ethyl-1,1-dimethyl-2,3-dihydro-1H-inden-4-yl]nicotinamide | 1 | 55 | |
| | | 0.5 | 30 | |
| | | 0.25 | 23 | |
| 1.008 | fluxapyroxad | 1 | 55 | |
| | | 0.25 | 15 | |
| 1.032 | 3-(difluoromethyl)-1-methyl-N-(1,1,3-trimethyl-2,3-dihydro-1H-inden-4-yl)-1H-pyrazole-4-carboxamide | 1 | 15 | |
| | | 0.5 | 0 | |
| | | 0.25 | 15 | |
| (I-3) + 1.008 1:1 | | 0.25 + 0.25 | 45 | 28 |
| (I-3) + 1.032 1:1 | | 0.5 + 0.5 | 60 | 45 |
| (I-4) + 1.008 2:1 | | 0.5 + 0.25 | 70 | 41 |
| (I-4) + 1.008 1:1 | | 1 + 1 | 88 | 80 |
| (I-4) + 1.008 1:2 | | 0.5 + 1 | 80 | 69 |
| (I-4) + 1.008 1:4 | | 0.25 + 1 | 75 | 65 |
| (I-4) + 1.032 4:1 | | 1 + 0.25 | 85 | 62 |
| (I-4) + 1.032 2:1 | | 1 0.5 | 65 | 55 |
| (I-4) + 1.032 1:1 | | 1 + 1 | 75 | 62 |

TABLE-continued in vivo preventive test on Alternaria test (tomatoes)

| Active compounds | | Application rate of active compound in ppm a.i. | Efficacy in % found* | calc.** |
|---|---|---|---|---|
| (I-4) + 1.032 1:2 | | 0.5 + 1 | 65 | 41 |
| (I-4) + 1.032 1:4 | | 0.25 + 1 | 70 | 34 |
| (I-5) | 2-(difluoromethyl)-N-(1,1-dimethyl-3-propyl-2,3-dihydro-1H-inden-4-yl)nicotinamide | 1<br>0.5<br>0.25 | 15<br>8<br>0 | |
| (I-6) | 2-(difluoromethyl)-N-[(3R)-1,1-dimethyl-3-propyl-2,3-dihydro-1H-inden-4-yl]nicotinamide | 1<br>0.5<br>0.25 | 45<br>23<br>15 | |
| 1.008 | fluxapyroxad | 1<br>0.5<br>0.25 | 78<br>45<br>8 | |
| 1.032 | 3-(difluoromethyl)-1-methyl-N-(1,1,3-trimethyl-2,3-dihydro-1H-inden-4-yl)-1H-pyrazole-4-carboxamide | 1<br>0.5<br>0.25 | 8<br>0<br>0 | |
| (I-5) + 1.008 4:1 | | 1 + 0.25 | 60 | 21 |
| (I-5) + 1.008 2:1 | | 1 + 0.5 | 78 | 53 |
| (I-5) + 1.008 1:1 | | 0.5 + 0.5 | 70 | 49 |
| (I-5) + 1.008 1:2 | | 0.25 + 0.5 | 68 | 45 |
| (I-5) + 1.008 1:4 | | 0.25 + 1 | 83 | 78 |
| (I-5) + 1.032 1:1 | | 1 + 1 | 45 | 21 |
| (I-5) + 1.032 1:2 | | 0.5 + 1 | 50 | 14 |
| (I-6) + 1.008 4:1 | | 1 + 0.25 | 73 | 49 |
| (I-6) + 1.008 2:1 | | 0.5 0.25 | 65 | 28 |
| (I-6) + 1.008 1:1 | | 0.5 + 0.5 | 75 | 57 |
| (I-6) + 1.008 1:2 | | 0.25 + 0.5 | 78 | 53 |
| (I-6) + 1.032 4:1 | | 1 + 0.25 | 55 | 45 |
| (I-6) + 1.032 2:1 | | 1 + 0.5 | 60 | 45 |
| (I-6) + 1.032 1:1 | | 0.5 + 0.5 | 55 | 23 |
| (I-6) + 1.032 1:2 | | 0.5 + 1 | 65 | 28 |
| (I-6) + 1.032 1:4 | | 0.25 + 1 | 55 | 21 |

*found = activity found
**calc. = activity calculated using Colby's formula

Example: In Vivo Preventive *Blumeria* Test (Barley)

| Solvent: | 49 parts by weight of N,N-dimethylacetamide |
|---|---|
| Emulsifier: | 1 part by weight of alkylaryl polyglycol ether |

To produce a suitable preparation of active compound, 1 part by weight of active compound or active compound combination is mixed with the stated amounts of solvent and emulsifier, and the concentrate is diluted with water to the desired concentration. To test for preventive activity, young plants are sprayed with the preparation of active compound or active compound combination at the stated rate of application. After the spray coating has been dried, the plants are dusted with spores of *Blumeria graminis* f.sp. *hordei*. The plants are placed in the greenhouse at a temperature of approximately 18° C. and a relative atmospheric humidity of approximately 80% to promote the development of mildew pustules.

The test is evaluated 7 days after the inoculation. 0% means an efficacy which corresponds to that of the untreated control, while an efficacy of 100% means that no disease is observed. The table below clearly shows that the observed activity of the active compound combination according to the invention is greater than the calculated activity, i.e. a synergistic effect is present.

TABLE in vivo preventive test on *Blumeria* test (barley)

| Active compounds | | Application rate of active compound in ppm a.i. | Efficacy in % found* | calc.** |
|---|---|---|---|---|
| (I-3) | 2-(difluoromethyl)-N-(3-ethyl-1,1-dimethyl-2,3-dihydro-1H-inden-4-yl)nicotinamide | 100<br>50 | 57<br>29 | |

TABLE-continued in vivo preventive test on *Blumeria* test (barley)

| | Active compounds | Application rate of active compound in ppm a.i. | Efficacy in % found* | Efficacy in % calc.** |
|---|---|---|---|---|
| 1.006 | fluopyram | 100 | 71 | |
| | | 50 | 29 | |
| (I-3) + 1.006 2:1 | | 100 + 50 | 86 | 69 |
| (I-3) + 1.006 1:1 | | 50 + 50 | 71 | 49 |
| (I-3) + 1.006 1:2 | | 50 + 100 | 93 | 80 |
| (I-4) | 2-(difluoromethyl)-N-[(3R)-3-ethyl-1,1-dimethyl-2,3-dihydro-1H-inden-4-yl]nicotinamide | 25 | 0 | |
| 1.006 | fluopyram | 50 | 0 | |
| (I-4) + 1.006 1:2 | | 25 + 50 | 50 | 0 |
| (I-6) | 2-(difluoromethyl)-N-[(3R)-1,1-dimethyl-3-propyl-2,3-dihydro-1H-inden-4-yl]nicotinamide | 50 | 40 | |
| 1.006 | fluopyram | 50 | 80 | |
| (I-6) + 1.006 1:1 | | 50 + 50 | 95 | 88 |

*found = activity found
**calc. = activity calculated using Colby's formula

Example: In Vivo Preventive Test on *Botrytis* Test (Beans)

| Solvent: | 24.5 parts by weight of acetone |
| | 24.5 parts by weight of dimethylacetamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration. To test for preventive activity, young plants are sprayed with the preparation of active compound. After the spray coating has dried on, 2 small pieces of agar covered with growth of *Botrytis cinerea* are placed on each leaf. The inoculated plants are placed in a darkened chamber at 20° C. and a relative atmospheric humidity of 100%.

2 days after the inoculation, the size of the lesions on the leaves is evaluated. 0% means an efficacy which corresponds to that of the untreated control, while an efficacy of 100% means that no disease is observed. The table below clearly shows that the observed activity of the active compound combination according to the invention is greater than the calculated activity, i.e. a synergistic effect is present.

TABLE in vivo preventive test on *Botrytis* test (beans)

| | Active compounds | Application rate of active compound in ppm a.i. | Efficacy in % found* | Efficacy in % calc.** |
|---|---|---|---|---|
| (I-3) | 2-(difluoromethyl)-N-(3-ethyl-1,1-dimethyl-2,3-dihydro-1H-inden-4-yl)nicotinamide | 1 | 0 | |
| | | 0.5 | 4 | |
| | | 0.25 | 0 | |
| 1.008 | fluxapyroxad | 1 | 8 | |
| | | 0.5 | 15 | |
| 1.032 | 3-(difluoromethyl)-1-methyl-N-(1,1,3-trimethyl-2,3-dihydro-1H-inden-4-yl)-1H-pyrazole-4-carboxamide | 1 | 14 | |
| | | 0.5 | 0 | |
| | | 0.25 | 18 | |
| (I-3) + 1.008 2:1 | | 1 + 0.5 | 45 | 15 |
| (I-3) + 1.008 1:1 | | 1 + 1 | 45 | 8 |
| (I-3) + 1.032 4:1 | | 1 + 0.25 | 50 | 18 |
| (I-3) + 1.032 2:1 | | 1 0.5 | 45 | 0 |
| (I-3) + 1.032 1:1 | | 1 + 1 | 50 | 14 |
| (I-3) + 1.032 1:2 | | 0.5 + 1 | 50 | 17 |
| (I-3) + 1.032 1:4 | | 0.25 + 1 | 45 | 14 |
| (I-5) | 2-(difluoromethyl)-N-(1,1-dimethyl-3-propyl-2,3-dihydro-1H-inden-4-yl)nicotinamide | 1 | 0 | |
| (I-6) | 2-(difluoromethyl)-N-[(3R)-1,1-dimethyl-3-propyl-2,3-dihydro-1H-inden-4-yl]nicotinamide | 1 | 0 | |
| | | 0.5 | 0 | |
| | | 0.25 | 0 | |
| 1.008 | fluxapyroxad | 1 | 0 | |
| | | 0.5 | 0 | |

TABLE-continued in vivo preventive test on *Botrytis* test (beans)

| | Active compounds | Application rate of active compound in ppm a.i. | Efficacy in % found* | calc.** |
|---|---|---|---|---|
| 1.032 | 3-(difluoromethyl)-1-methyl-N-(1,1,3-trimethyl-2,3-dihydro-1H-inden-4-yl)-1H-pyrazole-4-carboxamide | 1 | 0 | |
| (I-5) + 1.008 2:1 | | 1 + 0.5 | 51 | 0 |
| (I-5) + 1.008 1:1 | | 1 + 1 | 43 | 0 |
| (I-6) + 1.008 2:1 | | 1 + 0.5 | 59 | 0 |
| (I-6) + 1.008 1:1 | | 1 + 1 | 59 | 0 |
| (I-6) + 1.008 1:2 | | 0.25 + 0.5 | 60 | 0 |
| (I-6) + 1.032 1:2 | | 0.5 + 1 | 66 | 0 |

*found = activity found
**calc. = activity calculated using Colby's formula

Example: In Vivo Preventive *Leptosphaeria nodorum* Test (Wheat)

| Solvent: | 49 parts by weight of N,N-dimethylacetamide |
|---|---|
| Emulsifier: | 1 part by weight of alkylaryl polyglycol ether |

To produce a suitable preparation of active compound, 1 part by weight of active compound or active compound combination is mixed with the stated amounts of solvent and emulsifier, and the concentrate is diluted with water to the desired concentration. To test for preventive activity, young plants are sprayed with the preparation of active compound or active compound combination at the stated rate of application. After the spray coating has been dried, the plants are sprayed with a spore suspension of *Leptosphaeria nodorum*. The plants remain for 48 hours in an incubation cabinet at approximately 20° C. and a relative atmospheric humidity of approximately 100%. The plants are placed in the greenhouse at a temperature of approximately 25° C. and a relative atmospheric humidity of approximately 80%.

The test is evaluated 8 days after the inoculation. 0% means an efficacy which corresponds to that of the untreated control, while an efficacy of 100% means that no disease is observed. The table below clearly shows that the observed activity of the active compound combination according to the invention is greater than the calculated activity, i.e. a synergistic effect is present.

Example: In Vivo Preventive Test on *Phakopsora* Test (Soybeans)

| Solvent: | 24.5 parts by weight of acetone |
|---|---|
| | 24.5 parts by weight of dimethylacetamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration. To test for preventive activity, young plants are sprayed with the preparation of active compound at the stated rate of application. After the spray coating has dried on, the plants are inoculated with an aqueous spore suspension of the causal agent of soybean rust (*Phakopsora pachyrhizi*) and stay for 24 h without light in an incubation cabinet at approximately 24° C. and a relative atmospheric humidity of 95%. The plants remain in the incubation cabinet at approximately 24° C. and a relative atmospheric humidity of approximately 80% and a day/night interval of 12h.

The test is evaluated 7 days after the inoculation. 0% means an efficacy which corresponds to that of the untreated control, while an efficacy of 100% means that no disease is observed. The table below clearly shows that the observed activity of the active compound combination according to the invention is greater than the calculated activity, i.e. a synergistic effect is present.

TABLE in vivo preventive test on *Leptosphaeria nodorum* test (wheat)

| | Active compounds | Application rate of active compound in ppm a.i. | Efficacy in % found* | calc.** |
|---|---|---|---|---|
| (I-4) | 2-(difluoromethyl)-N-[(3R)-3-ethyl-1,1-dimethyl-2,3-dihydro-1H-inden-4-yl]nicotinamide | 25 | 0 | |
| 1.006 | fluopyram | 25 | 14 | |
| | | 12.5 | 14 | |
| (I-4) + 1.006 2:1 | | 25 + 12.5 | 43 | 14 |
| (I-4) + 1.006 1:1 | | 25 + 25 | 43 | 14 |

*found = activity found
**calc. = activity calculated using Colby's formula

TABLE in vivo preventive test on *Phakopsora* test (soybeans)

| | Active compounds | Application rate of active compound in ppm a.i. | Efficacy in % found* | Efficacy in % calc.** |
|---|---|---|---|---|
| (I-3) | 2-(difluoromethyl)-N-(3-ethyl-1,1-dimethyl-2,3-dihydro-1H-inden-4-yl)nicotinamide | 0.5 | 71 | |
| | | 0.25 | 24 | |
| (I-4) | 2-(difluoromethyl)-N-[(3R)-3-ethyl-1,1-dimethyl-2,3-dihydro-1H-inden-4-yl]nicotinamide | 1 | 87 | |
| | | 0.25 | 35 | |
| 1.008 | fluxapyroxad | 1 | 0 | |
| | | 0.5 | 0 | |
| | | 0.25 | 9 | |
| 1.032 | 3-(difluoromethyl)-1-methyl-N-(1,1,3-trimethyl-2,3-dihydro-1H-inden-4-yl)-1H-pyrazole-4-carboxamide | 1 | 0 | |
| | | 0.5 | 0 | |
| | | 0.25 | 0 | |
| (I-3) + 1.008 1:1 | | 0.5 + 0.5 | 76 | 71 |
| (I-3) + 1.032 1:1 | | 0.5 + 0.5 | 91 | 71 |
| (I-3) + 1.032 1:2 | | 0.5 + 1 | 87 | 71 |
| (I-3) + 1.032 1:4 | | 0.25 + 1 | 74 | 24 |
| (I-4) + 1.008 4:1 | | 1 + 0.25 | 99 | 88 |
| (I-4) + 1.008 2:1 | | 1 + 0.5 | 99 | 87 |
| (I-4) + 1.008 1:1 | | 0.25 + 0.25 | 71 | 41 |
| (I-4) + 1.008 1:4 | | 0.25 + 1 | 75 | 34 |
| (I-4) + 1.032 2:1 | | 1 0.5 | 94 | 87 |
| (I-4) + 1.032 1:1 | | 0.25 + 0.25 | 81 | 35 |
| (I-4) + 1.032 1:2 | | 0.25 + 0.5 | 74 | 35 |
| (I-4) + 1.032 1:4 | | 0.25 + 1 | 53 | 35 |
| (I-5) | 2-(difluoromethyl)-N-(1,1-dimethyl-3-propyl-2,3-dihydro-1H-inden-4-yl)nicotinamide | 1 | 85 | |
| | | 0.5 | 84 | |
| | | 0.25 | 78 | |
| (I-6) | 2-(difluoromethyl)-N-[(3R)-1,1-dimethyl-3-propyl-2,3-dihydro-1H-inden-4-yl]nicotinamide | 0.5 | 92 | |
| 1.008 | fluxapyroxad | 0.5 | 0 | |
| | | 0.25 | 0 | |
| 1.032 | 3-(difluoromethyl)-1-methyl-N-(1,1,3-trimethyl-2,3-dihydro-1H-inden-4-yl)-1H-pyrazole-4-carboxamide | 0.25 | 0 | |
| (I-5) + 1.008 4:1 | | 1 + 0.25 | 95 | 85 |
| (I-5) + 1.008 2:1 | | 0.5 + 0.25 | 92 | 84 |
| (I-5) + 1.008 1:1 | | 0.25 + 0.25 | 91 | 78 |
| (I-5) + 1.008 1:2 | | 0.25 + 0.5 | 92 | 78 |
| (I-5) + 1.032 4:1 | | 1 + 0.25 | 96 | 85 |
| (I-5) + 1.032 2:1 | | 0.5 + 0.25 | 95 | 84 |
| (I-5) + 1.032 1:1 | | 0.25 + 0.25 | 95 | 78 |
| (I-6) + 1.032 2:1 | | 0.5 + 0.25 | 97 | 92 |

*found = activity found
**calc. = activity calculated using Colby's formula

Example: In Vivo Preventive *Puccinia Triticina* Test (Wheat)

| Solvent: | 49 parts by weight of N,N-dimethylacetamide |
|---|---|
| Emulsifier: | 1 part by weight of alkylaryl polyglycol ether |

To produce a suitable preparation of active compound, 1 part by weight of active compound or active compound combination is mixed with the stated amounts of solvent and emulsifier, and the concentrate is diluted with water to the desired concentration. To test for preventive activity, young plants are sprayed with the preparation of active compound or active compound combination at the stated rate of application. After the spray coating has been dried, the plants are sprayed with a spore suspension of *Puccinia triticina*. The plants remain for 48 hours in an incubation cabinet at approximately 20° C. and a relative atmospheric humidity of approximately 100%. The plants are placed in the greenhouse at a temperature of approximately 20° C. and a relative atmospheric humidity of approximately 80%.

The test is evaluated 8 days after the inoculation. 0% means an efficacy which corresponds to that of the untreated control, while an efficacy of 100% means that no disease is observed. The table below clearly shows that the observed activity of the active compound combination according to the invention is greater than the calculated activity, i.e. a synergistic effect is present.

TABLE in vivo preventive test on *Puccinia triticina* test (wheat)

| | Active compounds | Application rate of active compound in ppm a.i. | Efficacy in % found* | calc.** |
|---|---|---|---|---|
| (I-4) | 2-(difluoromethyl)-N-[(3R)-3-ethyl-1,1-dimethyl-2,3-dihydro-1H-inden-4-yl]nicotinamide | 12.5 | 80 | |
| (I-5) | 2-(difluoromethyl)-N-(1,1-dimethyl-3-propyl-2,3-dihydro-1H-inden-4-yl)nicotinamide | 25 | 50 | |
| 1.006 | fluopyram | 50 | 10 | |
| | | 12.5 | 0 | |
| (I-4) + 1.006 1:1 | | 12.5 + 12.5 | 90 | 80 |
| (I-5) + 1.006 1:2 | | 25 + 50 | 95 | 55 |
| (I-6) | 2-(difluoromethyl)-N-[(3R)-1,1-dimethyl-3-propyl-2,3-dihydro-1H-inden-4-yl]nicotinamide | 25 | 90 | |
| 1.006 | fluopyram | 50 | 30 | |
| (I-6) + 1.006 1:2 | | 25 + 50 | 100 | 93 |

*found = activity found
**calc. = activity calculated using Colby's formula

Example: In Vivo Preventive *Pyrenophora Teres* Test (Barley)

| Solvent: | 49 parts by weight of N,N-dimethylacetamide |
|---|---|
| Emulsifier: | 1 part by weight of alkylaryl polyglycol ether |

To produce a suitable preparation of active compound, 1 part by weight of active compound or active compound combination is mixed with the stated amounts of solvent and emulsifier, and the concentrate is diluted with water to the desired concentration. To test for preventive activity, young plants are sprayed with the preparation of active compound or active compound combination at the stated rate of application. After the spray coating has been dried, the plants are sprayed with a spore suspension of *Pyrenophora teres*. The plants remain for 48 hours in an incubation cabinet at approximately 20° C. and a relative atmospheric humidity of approximately 100%. The plants are placed in the greenhouse at a temperature of approximately 20° C. and a relative atmospheric humidity of approximately 80%.

The test is evaluated 8 days after the inoculation. 0% means an efficacy which corresponds to that of the untreated control, while an efficacy of 100% means that no disease is observed. The table below clearly shows that the observed activity of the active compound combination according to the invention is greater than the calculated activity, i.e. a synergistic effect is present.

TABLE in vivo preventive test on *Pyrenophora teres* test (barley)

| | Active compounds | Application rate of active compound in ppm a.i. | Efficacy in % found* | calc.** |
|---|---|---|---|---|
| (I-3) | 2-(difluoromethyl)-N-(3-ethyl-1,1-dimethyl-2,3-dihydro-1H-inden-4-yl)nicotinamide | 100 | 50 | |
| | | 50 | 38 | |
| | | 25 | 13 | |
| (I-4) | 2-(difluoromethyl)-N-[(3R)-3-ethyl-1,1-dimethyl-2,3-dihydro-1H-inden-4-yl]nicotinamide | 50 | 33 | |
| | | 25 | 22 | |
| | | 12.5 | 22 | |
| (I-5) | 2-(difluoromethyl)-N-(1,1-dimethyl-3-propyl-2,3-dihydro-1H-inden-4-yl)nicotinamide | 100 | 50 | |
| | | 50 | 0 | |
| | | 25 | 0 | |
| 1.006 | fluopyram | 50 | 75 | |
| | | 12.5 | 33 | |
| (I-3) + 1.006 2:1 | | 100 + 50 | 100 | 88 |
| (I-3) + 1.006 1:1 | | 50 + 50 | 100 | 84 |
| (I-3) + 1.006 1:2 | | 25 + 50 | 94 | 78 |
| (I-4) + 1.006 2:1 | | 25 + 12.5 | 56 | 48 |
| (I-4) + 1.006 1:1 | | 12.5 + 12.5 | 56 | 48 |
| (I-4) + 1.006 1:2 | | 25 + 50 | 89 | 83 |
| (I-5) + 1.006 2:1 | | 100 + 50 | 94 | 88 |
| (I-5) + 1.006 1:1 | | 50 + 50 | 88 | 75 |
| (I-5) + 1.006 1:2 | | 25 + 50 | 88 | 75 |

*found = activity found
**calc. = activity calculated using Colby's formula

Example: In Vivo Preventive *Septoria tritici* Test (Wheat)

| Solvent: | 49 parts by weight of N,N-dimethylacetamide |
|---|---|
| Emulsifier: | 1 part by weight of alkylaryl polyglycol ether |

To produce a suitable preparation of active compound, 1 part by weight of active compound or active compound combination is mixed with the stated amounts of solvent and emulsifier, and the concentrate is diluted with water to the desired concentration. To test for preventive activity, young plants are sprayed with the preparation of active compound or active compound combination at the stated rate of application. After the spray coating has been dried, the plants are sprayed with a spore suspension of *Septoria tritici*. The plants remain for 48 hours in an incubation cabinet at approximately 20° C. and a relative atmospheric humidity of approximately 100% and afterwards for 60 hours at approximately 15° C. in a translucent incubation cabinet at a relative atmospheric humidity of approximately 100%. The plants are placed in the greenhouse at a temperature of approximately 15° C. and a relative atmospheric humidity of approximately 80%.

The test is evaluated 21 days after the inoculation. 0% means an efficacy which corresponds to that of the untreated control, while an efficacy of 100% means that no disease is observed. The table below clearly shows that the observed activity of the active compound combination according to the invention is greater than the calculated activity, i.e. a synergistic effect is present.

TABLE in vivo preventive test on *Septoria tritici* test (wheat)

| | Active compounds | Application rate of active compound in ppm a.i. | Efficacy in % found* | calc.** |
|---|---|---|---|---|
| (I-3) | 2-(difluoromethyl)-N-(3-ethyl-1,1-dimethyl-2,3-dihydro-1H-inden-4-yl)nicotinamide | 50 | 83 | |
| | | 25 | 17 | |
| 1.006 | fluopyram | 25 | 17 | |
| (I-3) + 1.006 2:1 | | 50 + 25 | 100 | 86 |
| (I-3) + 1.006 1:1 | | 25 + 25 | 67 | 31 |

*found = activity found
**calc. = activity calculated using Colby's formula

Example: In Vivo Preventive Test on *Venturia* Test (Apples)

| Solvent: | 24.5 parts by weight of acetone |
|---|---|
| | 24.5 parts by weight of dimethylacetamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration. To test for preventive activity, young plants are sprayed with the preparation of active compound at the stated rate of application. After the spray coating has dried on, the plants are inoculated with an aqueous conidia suspension of the causal agent of apple scab (*Venturia inaequalis*) and then remain for 1 day in an incubation cabinet at approximately 20° C. and a relative atmospheric humidity of 100%. The plants are then placed in a greenhouse at approximately 21° C. and a relative atmospheric humidity of approximately 90%.

The test is evaluated 10 days after the inoculation. 0% means an efficacy which corresponds to that of the untreated control, while an efficacy of 100% means that no disease is observed. The table below clearly shows that the observed activity of the active compound combination according to the invention is greater than the calculated activity, i.e. a synergistic effect is present.

TABLE in vivo preventive test on *Venturia* test (apples)

| | Active compounds | Application rate of active compound in ppm a.i. | Efficacy in % found* | calc.** |
|---|---|---|---|---|
| (I-3) | 2-(difluoromethyl)-N-(3-ethyl-1,1-dimethyl-2,3-dihydro-1H-inden-4-yl)nicotinamide | 0.5 | 11 | |

TABLE-continued

| | | Application rate of active compound in ppm | Efficacy in % | |
|---|---|---|---|---|
| Active compounds | | a.i. | found* | calc.** |
| (I-4) | 2-(difluoromethyl)-N-[(3R)-3-ethyl-1,1-dimethyl-2,3-dihydro-1H-inden-4-yl]nicotinamide | 1<br>0.5 | 21<br>12 | |
| 1.008 | fluxapyroxad | 1<br>0.5 | 20<br>8 | |
| 1.032 | 3-(difluoromethyl)-1-methyl-N-(1,1,3-trimethyl-2,3-dihydro-1H-inden-4-yl)-1H-pyrazole-4-carboxamide | 1 | 26 | |
| (I-3) + 1.008 1:2 | | 0.5 + 1 | 46 | 29 |
| (I-4) + 1.008 2:1 | | 1 + 0.5 | 52 | 27 |
| (I-4) + 1.008 1:2 | | 0.5 + 1 | 46 | 29 |
| (I-4) + 1.032 1:1 | | 1 + 1 | 68 | 42 |
| (I-5) | 2-(difluoromethyl)-N-(1,1-dimethyl-3-propyl-2,3-dihydro-1H-inden-4-yl)nicotinamide | 1<br>0.5<br>0.25 | 15<br>0<br>0 | |
| (I-6) | 2-(difluoromethyl)-N-[(3R)-1,1-dimethyl-3-propyl-2,3-dihydro-1H-inden-4-yl]nicotinamide | 1<br>0.5<br>0.25 | 10<br>5<br>0 | |
| 1.008 | fluxapyroxad | 1<br>0.5 | 55<br>10 | |
| 1.032 | 3-(difluoromethyl)-1-methyl-N-(1,1,3-trimethyl-2,3-dihydro-1H-inden-4-yl)-1H-pyrazole-4-carboxamide | 1<br>0.5 | 0<br>0 | |
| (I-5) + 1.008 1:1 | | 1 + 1 | 90 | 62 |
| (I-5) + 1.008 1:2 | | 0.5 + 1 | 94 | 55 |
| (I-5) + 1.032 1:1 | | 1 + 1 | 45 | 15 |
| (I-5) + 1.032 1:2 | | 0.5 + 1 | 43 | 0 |
| (I-5) + 1.032 1:4 | | 0.25 + 1 | 57 | 0 |
| (I-6) + 1.008 2:1 | | 1 + 0.5 | 93 | 19 |
| (I-6) + 1.008 1:1 | | 1 + 1 | 94 | 60 |
| (I-6) + 1.008 1:2 | | 0.5 + 1 | 63 | 57 |
| (I-6) + 1.008 1:4 | | 0.25 + 1 | 80 | 55 |
| (I-6) + 1.032 2:1 | | 1 + 0.5 | 42 | 10 |
| (I-6) + 1.032 1:2 | | 0.5 + 1 | 58 | 5 |

*found = activity found
**calc. = activity calculated using Colby's formula

The invention claimed is:

1. A composition comprising at least one compound A selected from the group consisting of:

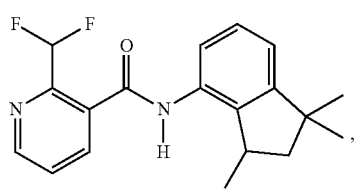
(I-1)

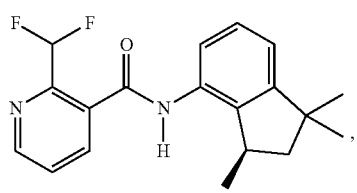
(I-2)

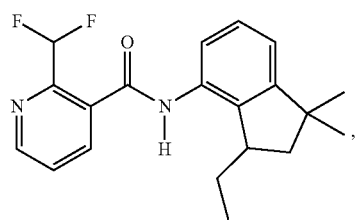
(I-3)

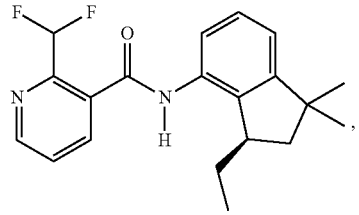
(I-4)

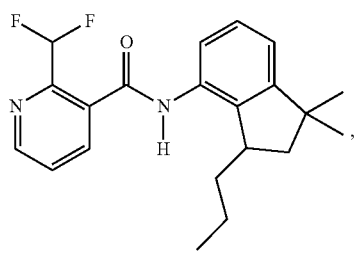 (I-5)

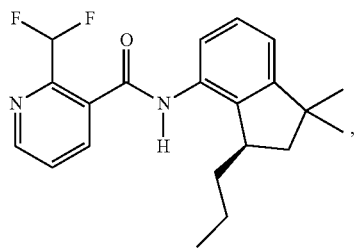 (I-6)

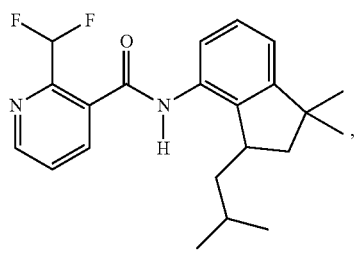 (I-7)

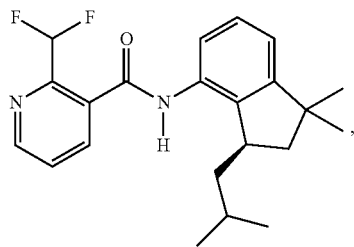 (I-8)

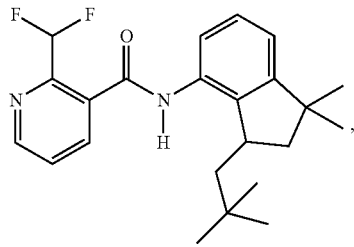 (I-9)

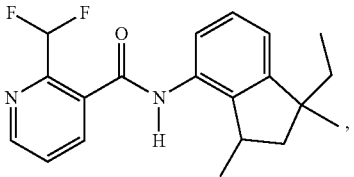 (I-10)

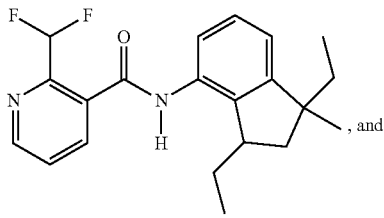 (I-11)

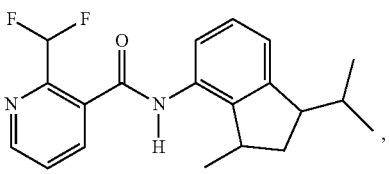 (I-12)

and (B) at least one further active compound selected from the group consisting of (1.006) fluopyram, (1.008) fluxapyroxad, and (1.032) 3-(difluoromethyl)-1-methyl-N-(1,1,3-trimethyl-2,3,-dihydro-1H-inden-4-yl)-1H-pyrazole-4-carboxamide.

2. A method for controlling phytopathogenic harmful fungi, comprising applying a composition according to claim 1 to the phytopathogenic harmful fungi and/or a habitat thereof.

3. A product for controlling phytopathogenic harmful fungi, comprising at least one composition according to claim 1, in addition to one or more extenders and/or surfactants.

4. A plant growth regular comprising a composition according to claim 1.

5. A process for producing a composition for controlling phytopathogenic harmful fungi, comprising mixing a composition according to claim 1 with one or more extenders and/or surfactants.

6. A method according to claim 2 comprising treatment of one or more transgenic plants.

7. A seed treated with composition according to claim 1.

8. The composition according to claim 1, wherein (B) comprises (1.006) fluopyram.

9. The composition according to claim 1, wherein (B) comprises (1.008) fluxapyroxad.

10. The composition according to claim 1, wherein (B) comprises (1.032) 3-(difluoromethyl)-1-methyl-N-(1,1,3-trimethyl-2,3,-dihydro-1H-inden-4-yl)-1H-pyrazole-4-carboxamide.

11. The composition according to claim 1, wherein the weight ratio of (A) to (B) is 25:1 to 1:25.

12. The composition according to claim 1, wherein the weight ratio of (A) to (B) is 10:1 to 1:10.

13. The composition according to claim 1, wherein the weight ratio of (A) to (B) is 5:1 to 1:5.

14. The composition according to claim 1, wherein (A) to (B) are present in amounts to provide synergisitc results.

15. The composition according to claim 1, wherein (A) comprises (I3), (I4), (I5), or (I6).

16. The composition according to claim 1, wherein (A) to (B) are the only agriculturally active components present in the composition.

* * * * *